US012774269B2

(12) United States Patent
Singh et al.

(10) Patent No.: US 12,774,269 B2
(45) Date of Patent: Oct. 27, 2026

(54) QUINOLONE COMPOUND IN SOLID FORMS AND PROCESSES FOR THE PREPARATION THEREOF

(71) Applicant: ZYDUS LIFESCIENCES LIMITED, Ahmedabad (IN)

(72) Inventors: Kumar Kamlesh Singh, Ahmedabad (IN); Rajiv Sharma, Ahmedabad (IN); Santosh Devidas Diwakar, Ahmedabad (IN); Jitendra Maganbhai Gajera, Ahmedabad (IN); Sumer Singh Chundawat, Ahmedabad (IN); Jayesh Anilkumar Sharma, Ahmedabad (IN)

(73) Assignee: ZYDUS LIFESCIENCES LIMITED, Gujarat (IN)

( * ) Notice: Subject to any disclaimer, the term of this patent is extended or adjusted under 35 U.S.C. 154(b) by 457 days.

(21) Appl. No.: 18/547,618

(22) PCT Filed: Mar. 17, 2022

(86) PCT No.: PCT/IB2022/052415
§ 371 (c)(1),
(2) Date: Aug. 23, 2023

(87) PCT Pub. No.: WO2022/195525
PCT Pub. Date: Sep. 22, 2022

(65) Prior Publication Data

US 2024/0300899 A1 Sep. 12, 2024

(30) Foreign Application Priority Data

Mar. 19, 2021 (IN) ............................ 202121011753

(51) Int. Cl.

| | |
|---|---|
| ***C07D 215/58*** | (2006.01) |
| ***A61K 31/4704*** | (2006.01) |
| ***A61P 3/00*** | (2006.01) |
| ***A61P 7/06*** | (2006.01) |
| ***C07D 215/56*** | (2006.01) |
| ***C07D 215/60*** | (2006.01) |

(52) U.S. Cl.
CPC ........ *C07D 215/60* (2013.01); *A61K 31/4704* (2013.01); *C07D 215/56* (2013.01); *C07D 215/58* (2013.01)

(58) Field of Classification Search
CPC ................ C07D 215/58; C07D 215/60; A61K 31/4704; A61P 3/00; A61P 7/06; C07B 2200/13
See application file for complete search history.

(56) References Cited

U.S. PATENT DOCUMENTS

| | | | | |
|---|---|---|---|---|
| 9,394,300 | B2 * | 7/2016 | Desai | A61P 7/06 |
| 2009/0124617 | A1 | 5/2009 | Watanuki et al. | |
| 2012/0245200 | A1 | 9/2012 | Ohara et al. | |
| 2019/0359574 | A1 | 11/2019 | Desai et al. | |

FOREIGN PATENT DOCUMENTS

WO 2014102818 A1 7/2014

OTHER PUBLICATIONS

Deven V. Parmar et al. "Outcomes of Desidustat Treatment in People with Anemia and Chronic Kidney Disease: A Phase 2 Study." Am J Nephrol, May 21, 2019 (May 21, 2019) Abstract, pp. 472-473, 475-476 Tables 1 and 2.

* cited by examiner

*Primary Examiner* — Brenda L Coleman

(74) *Attorney, Agent, or Firm* — Renner, Kenner, Greive, Bobak, Taylor & Weber Co. LPA

(57) ABSTRACT

The present invention relates to novel crystalline forms of a quinolone compound of Formula (I). The invention also relates to processes for the preparation crystalline forms of the compound of Formula (I). Further the disclosure provides a process for the preparation of compound of Formula (I), intermediates, impurities and pharmaceutical compositions thereof.

(I)

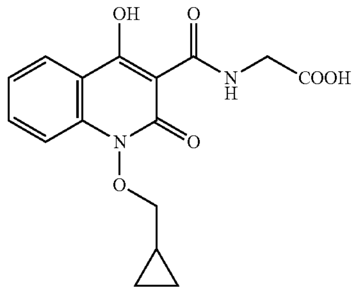

25 Claims, 2 Drawing Sheets

QUINOLONE COMPOUND IN SOLID FORMS AND PROCESSES FOR THE PREPARATION THEREOF

RELATED APPLICATION

Figure 1:
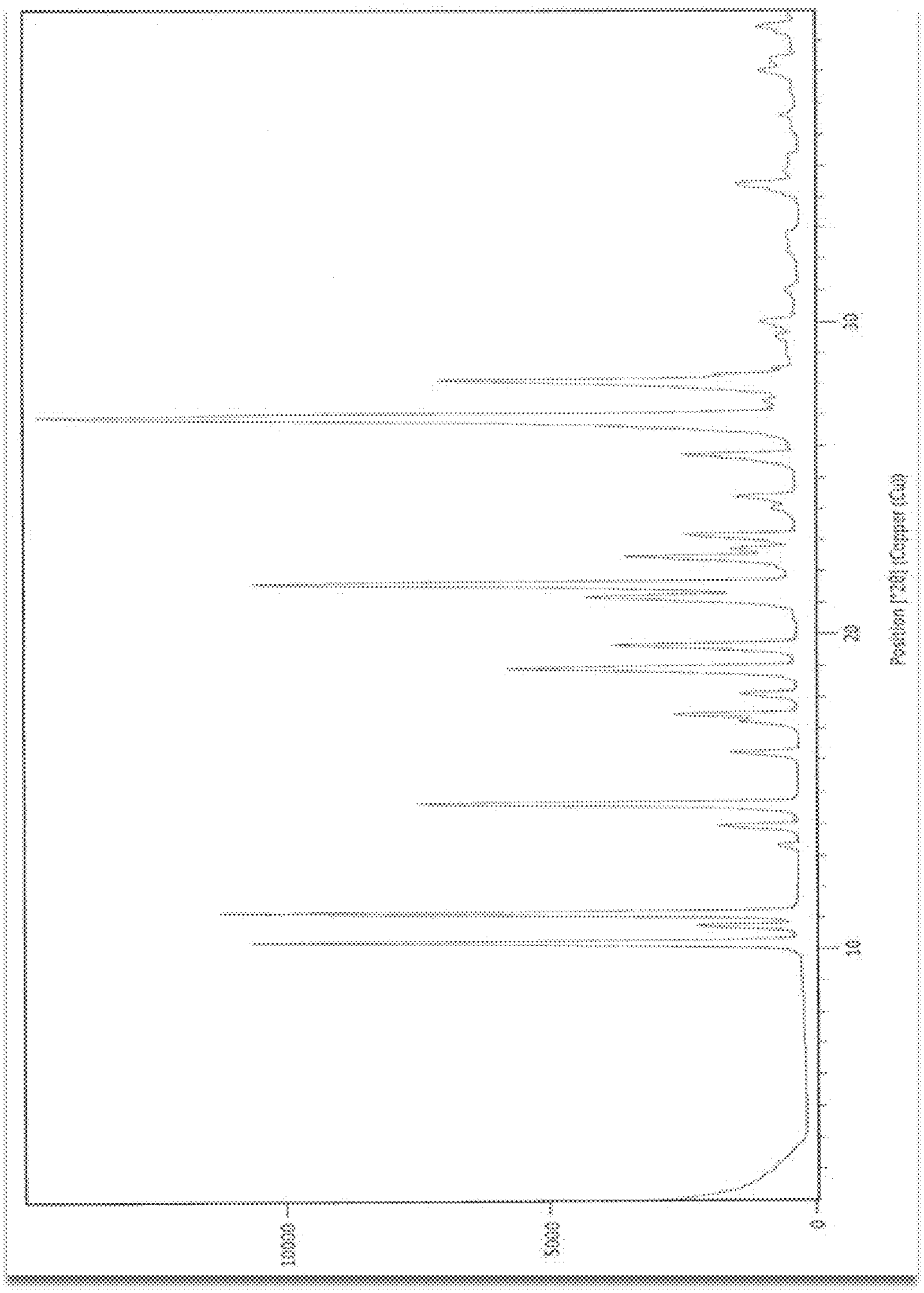

This application claims the benefit of Indian Provisional Patent Application No. 202121011753 filed on Mar. 19, 2021, the contents of which are incorporated herein by reference.

FIELD OF THE INVENTION

The invention relates to the field of pharmaceuticals. In particular, the invention relates to solid forms of a quinolone compound and processes for the preparation thereof.

BACKGROUND OF THE INVENTION

The following discussion of background is intended to present the invention in an appropriate technical context and allow its significance to be properly appreciated.

International (PCT) Publication No. WO 2014/102818 discloses quinoline derivatives, including (1-(cyclopropylmethoxy)-4-hydroxy-2-oxo-1,2-dihydroquinoline-3-carbonyl)glycine (the compound of Formula (I)), as Hypoxia-inducible factor (HIF) hydroxylases inhibitors having utility in any disease state where ischemia hypoxia and/or anemia plays a role.

(I)

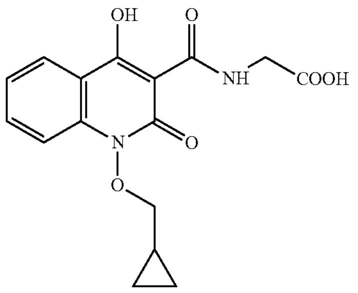

U.S. PG-Pub. No. 2019/0359574 discloses a process for the preparation of quinolone compounds, including the compound of Formula (I), and a crystalline form thereof.

The solid form of a compound plays a pivotal role in the formulation of pharmaceutical compositions. For example, different forms of a compound can have different physical properties (e.g., stability, dissolution rate, density, etc.) relating to their suitability for use in pharmaceutical compositions. Different polymorphic forms can also show different behavior with respect to their dissolution properties, flow properties, particle size distribution and chemical stability. Thus, having a suitable polymorphic form with desired properties is an important prerequisite during drug development.

The present invention provides the compound of Formula (I) in solid forms to aid in the development of pharmaceutical composition, and also an alternative process for the preparation of the compound of Formula (I), which is cost-efficient, scalable and environment friendly.

SUMMARY OF THE INVENTION

In one general aspect, there is provided crystalline forms of compound of Formula (I).

In another general aspect, there is provided processes for the preparation of crystalline forms of compound of Formula (I).

In another general aspect, there is provided a composition comprising the crystalline form of compound of Formula (I).

In another general aspect, there is provided a pharmaceutical composition comprising crystalline form of compound of Formula (I) and pharmaceutically acceptable excipient, diluents or carriers.

In another general aspect, there is provided a pharmaceutical composition comprising crystalline form of compound of Formula (I) useful in the treatment of conditions associated with anemia.

In another general aspect, there is provided a process for the preparation of a compound of Formula (I), the process comprising:

(a) reacting a compound of Formula (VII), (VII)

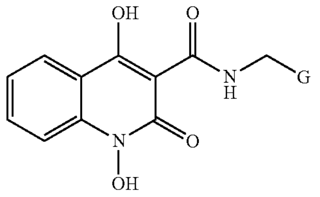

with a compound of Formula (VIII), (VIII)

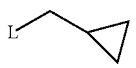

wherein,

L is a leaving group;

to obtain a compound of Formula (IX);

(IX)

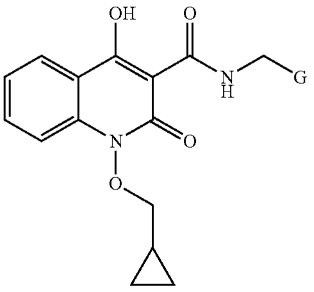

wherein,

G is selected from CN, —COORa and —CONRbRc,

Ra is selected from alkyl, cycloalkyl, heterocycloalkyl, aryl and heteroaryl; wherein Ra is optionally further substituted with one or more of chloro, bromo, iodo, cyano, hydroxy, nitro, amino, alkylamino, carbonyl, aminocarbonyl, thio, alkylthio, alkyl, cycloalkyl, heterocycloalkyl, aryl or heteroaryl, Rb and Rc each independently is hydrogen or Ra; and, (b) converting the compound of Formula (IX) to the compound of Formula (I).

In another general aspect, there is provided a compound of Formula (VII),

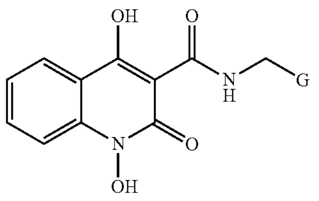

(VII)

wherein,

G is selected from CN, —COORa and —CONRbRc,

Ra is selected from alkyl, cycloalkyl, heterocycloalkyl, aryl and heteroaryl; wherein Ra is optionally further substituted with one or more of chloro, bromo, iodo, cyano, hydroxy, nitro, amino, alkylamino, carbonyl, aminocarbonyl, thio, alkylthio, alkyl, cycloalkyl, heterocycloalkyl, aryl or heteroaryl; and Rb and Rc each independently is hydrogen or Ra.

In another general aspect, there is provided a process for the preparation of a compound of Formula (VII),

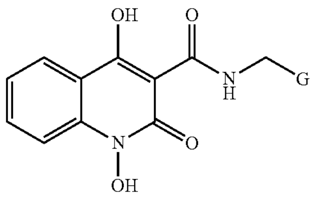

(VII)

the process comprising:

(a) converting a compound of Formula (IV),

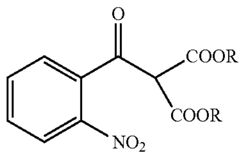

(IV)

to a compound of Formula (VI), and,

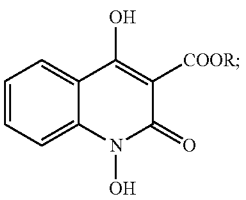

(VI)

(b) reacting the compound of Formula (VI) with a compound of Formula (X)

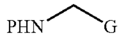

(X)

to obtain the compound of Formula (VII);

wherein, each R is independently selected from alkyl and aryl,

P is selected from hydrogen or amino protecting group; and

G is selected from CN, —COORa and —CONRbRc,

Ra is selected from alkyl, cycloalkyl, heterocycloalkyl, aryl and heteroaryl; wherein Ra is optionally further substituted with one or more of chloro, bromo, iodo, cyano, hydroxy, nitro, amino, alkylamino, carbonyl, aminocarbonyl, thio, alkylthio, alkyl, cycloalkyl, heterocycloalkyl, aryl or heteroaryl; and Rb and Rc each independently is hydrogen or Ra.

In another general aspect, there is provided a process for the preparation of a compound of Formula (I),

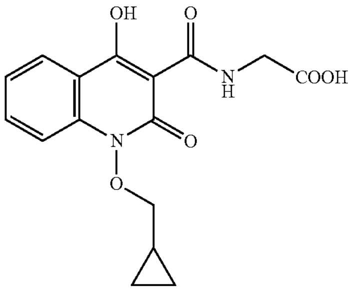

(I)

the process comprising:

(a) converting a compound of Formula (IV),

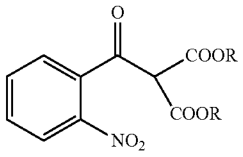

(IV)

to a compound of Formula (VI);

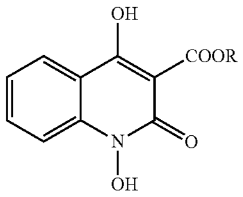

(VI)

(b) reacting the compound of Formula (VI) with a compound of Formula (X),

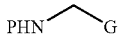

(X)

wherein,

P is selected from hydrogen or amino protecting group; to obtain a compound of Formula (VII);

(VII)

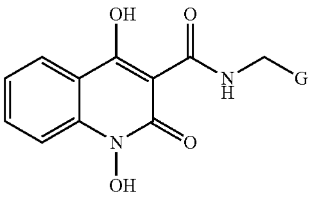

(c) reacting the compound of Formula (VII) with a compound of Formula (VIII), (VIII)

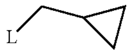

wherein, L is a leaving group, to obtain a compound of Formula (IX);

(IX)

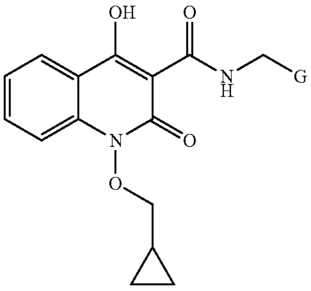

and, (d) converting the compound of Formula (IX) to the compound of Formula (I), wherein, each R is independently selected from alkyl and aryl, and G is selected from CN, —COORa and —CONRbRc, Ra is selected from alkyl, cycloalkyl, heterocycloalkyl, aryl and heteroaryl; wherein Ra is optionally further substituted with one or more of chloro, bromo, iodo, cyano, hydroxy, nitro, amino, alkylamino, carbonyl, aminocarbonyl, thio, alkylthio, alkyl, cycloalkyl, heterocycloalkyl, aryl or heteroaryl; and Rb and Rc each independently is hydrogen or Ra.

In another general aspect, there are provided compounds of Formulae A, B, C, D and E.

(A)

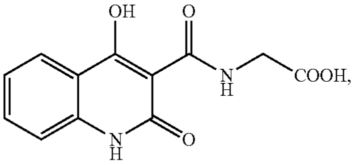

-continued (B)

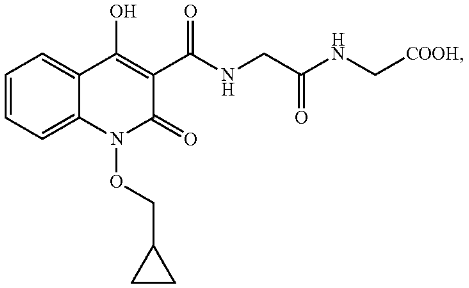

(C)

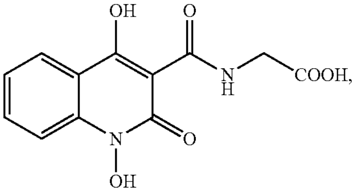

(D)

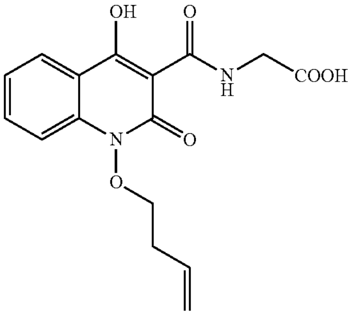

(E)

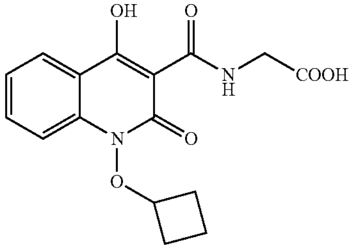

In another general aspect, there is provided compound of Formula (I) free from one or more of compounds of Formulae A, B, C, D or E.

In another general aspect, there is provided a composition comprising compound of Formula (I) free from one or more of compounds of Formulae A, B, C, D or E.

The crystalline forms of the compound of Formula (I) of the present invention may exhibit increased solubility and thermal stability; may provide better oral bioavailability and/or a better dissolution profile for a particular formulation; may also provide free-flowing easily filterable, and/or thermally stable characteristics that are suitable for use in particular formulations.

BRIEF DESCRIPTION OF THE ACCOMPANYING DRAWINGS

FIG. 1: Powder X-ray diffraction (XRD) pattern of crystalline form of compound of Formula (I) as prepared in example 1.

Figure 2:
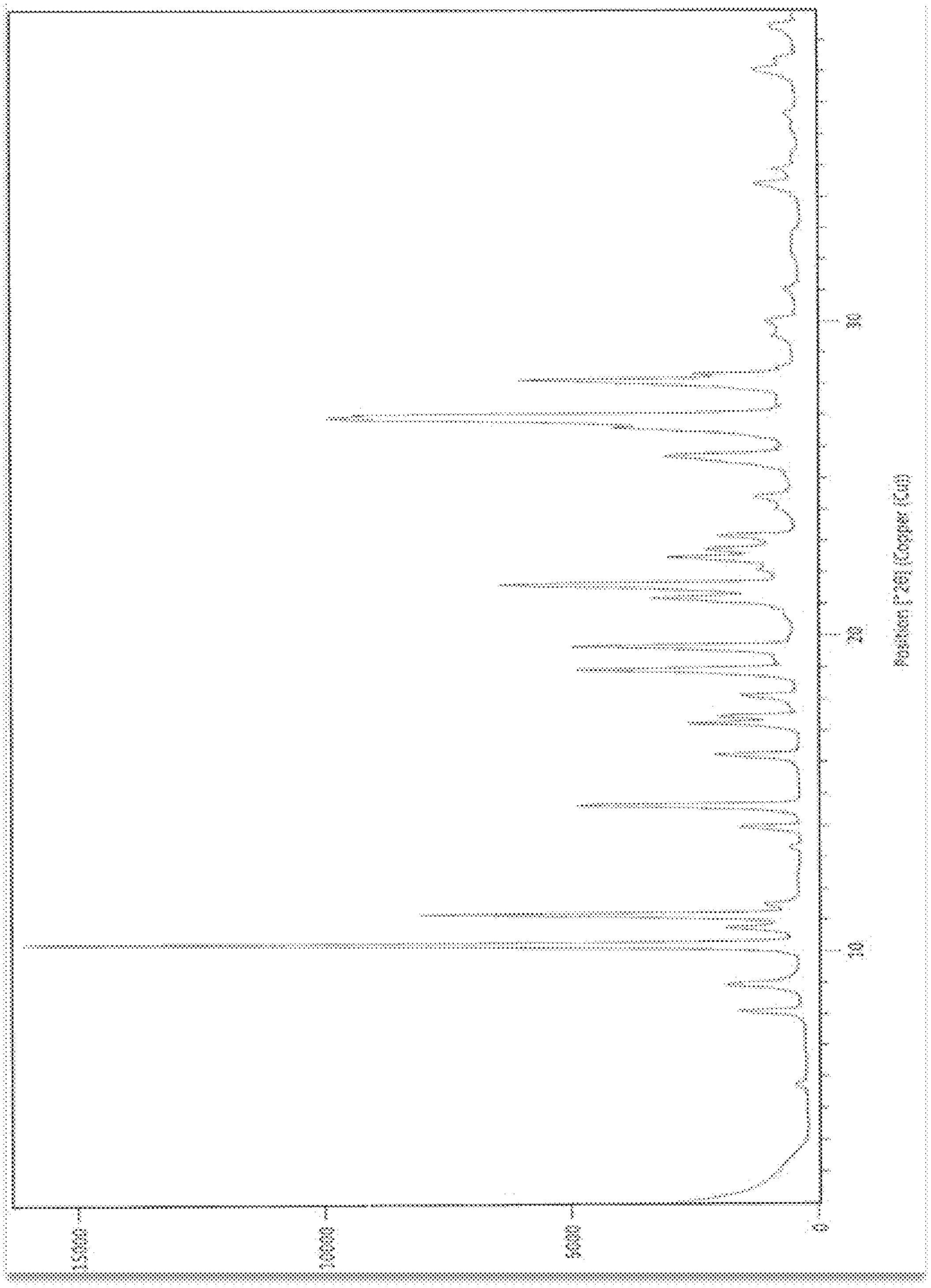

FIG. 2: Powder X-ray diffraction (XRD) pattern of crystalline form of compound of Formula (I) as prepared in example 2.

DETAILED DESCRIPTION OF THE INVENTION

The aforementioned general and further specific aspects of the invention are fulfilled by the description of the invention provided herein after. Detailed description of routine and conventional unit operations, which are easily understood by the skilled artisan, are not included herein. Such routine unit operations are to be construed as ordinarily understood and as routinely practiced by the person skilled in the field of the invention, unless otherwise specifically described.

The ranges recited herein also include the values denoted as the limits thereof. The numerical values recited as the limits are not to be construed as absolute values. Any value outside the recited ranges, wherein the difference between the values is insignificant considering the nature or the property of the variable to which the limit is applied, including any analytical variation in measuring those values, are also considered to be included within those ranges.

Undissolved solid and/or foreign particles, if any, can be removed before solid formation and/or solvent removal. A suitable technique useful for removal of solids can be selected from, but not limited to, filtration, decantation and centrifugation.

The term "alkyl" as used herein, unless otherwise specifically described, refers to a straight or branched chain hydrocarbon containing from 1 to 15 carbon atoms, one or more of which may be substituted with hetero atom(s) independently selected from nitrogen, oxygen, and sulfur. The non-limiting examples of alkyl group includes methyl, ethyl, n-propyl, isopropyl, n-butyl, isobutyl, n-pentyl, etc.

The numerical in phrases like "$C_{1-4}$ alkyl", refers that there are 1 to 4 carbon atoms in the alky chain.

The term "cycloalkyl" as used herein, unless otherwise specifically described, refers to a substituted or unsubstituted cyclic hydrocarbon ring containing from 3 to 15 carbon atoms; and which can be mono-, di-, tri- or tetracyclic. The non-limiting examples of cycloalkyl group includes cyclopropyl, cyclobutyl, cyclopentyl, cyclohexyl, etc.

The term "heterocycloalkyl" as used herein, unless otherwise specifically described, refers to a cycloalkyl ring containing one or more hetero atom(s) independently selected from nitrogen, oxygen, and sulfur. The non-limiting examples of heterocycloalkyl group includes pyrrolidinyl, piperidinyl, piperazinyl, morpholinyl, thiomorpholine and 1,3-oxazine.

The term "aryl" as used herein, unless otherwise specifically described, refers to a substituted or unsubstituted aromatic cyclic hydrocarbon ring containing 6 to 15 carbon atoms; and which can be monocyclic phenyl ring or polycyclic fused ring systems. The non-limiting examples of aryl group includes phenyl, naphthyl, indanyl (for e.g. 1-indanyl, 5-indanyl), indenyl, anthracenyl and phenanthrenyl.

The term "heteroaryl" as used herein, unless otherwise specifically described, refers to 5 to 10 membered aromatic ring containing one or more hetero atom(s) independently selected from nitrogen, oxygen, and sulfur. The non-limiting examples of heteroaryl group includes oxazolyl, isoxazolyl, imidazolyl, furyl, pyrrolyl, triazolyl, triazinyl, tetrazoyl, thienyl, thiazolyl, isothiazolyl, pyridyl, pyrimidinyl, pyrazinyl, pyridazinyl, benzofuranyl, benzothiazolyl, etc.

The terms "protected" and "protecting group" as used herein, are in their ordinary meaning as used in the field of the invention, unless otherwise specifically described.

In general, the terms "reacting", "treating" and "condensing" are generally interchangeable and are used in their ordinary meaning as they are used in the field of the invention, unless specifically defined otherwise.

The terms "isolating", "obtaining" and "purifying" are generally interchangeable, and include but not specifically limited to decantation, extraction, filtration, evaporation, lyophilisation, spray drying, crystallization, recrystallization or chromatographic operations.

The term "converting" means reacting the compound to which it refers with another compound and/or reagent; and/or subjecting it to condition(s) where it transforms to another compound as a result of such treatment.

The term "free from" means impurity content within the permissible ICH limits suitable for pharmaceutical preparations. In particular, the impurity content for each of the impurities of compound of Formulae A, B, C, D, and E by area percentage of HPLC is about 0.15% or less, more particularly, about 0.10% or less, or more particularly not detected by HPLC method of analysis.

The term "relative intensity" refers to the intensity of a peak with respect to the intensity of the strongest peak in the X-ray powder diffraction (XRPD) pattern which is regarded as 100%.

The term "pharmaceutically acceptable" as used herein means useful in preparing a pharmaceutical composition that is generally non-toxic and is not biologically undesirable, and is acceptable for veterinary or human pharmaceutical use.

The term "composition" as used herein means a physical mixture of two or more components.

The term "pharmaceutical composition" as used herein means a drug product comprising the active ingredient(s) & pharmaceutically acceptable excipient(s), as well as any product, which results, directly or indirectly, from combination, complexation or aggregation of any two or more of the ingredients including an active ingredient.

The term "stable" as used herein refers to the polymorphic form stability and chemical stability. The product(s) obtained may further be transformed to any other physical forms thereof which includes but not specifically limited to salt(s), solvate(s), hydrate(s), co-crystal(s) and solid dispersion(s) in either crystalline or amorphous forms and/or subjected to further physical processing like milling, sifting or other suitable powder processing techniques to adjust the particle size of the product to desired levels.

The product(s) obtained may further be dried additionally to achieve desired level of moisture and/or residual solvents.

Solid Forms

In one general aspect, there is provided solid form of compound of Formula (I). In particular, the solid form of compound of Formula (I) is crystalline.

The crystalline forms of the present invention were found to be stable upon storage and were non-hygroscopic.

The crystalline form of the compound of Formula (I) is characterized by an X-ray powder diffraction pattern having peaks expressed in degrees 2θ±0.2° at 11.1°, 18.9° and 21.6° (±0.2° 2θ).

In another general aspect, the crystalline form of compound of Formula (I) is characterized by X-ray powder diffraction pattern having peaks expressed in degrees 2θ±0.2° at 10.2°, 11.1°, and 21.6°; or 8.9°, 11.1°, and 21.6°; or 10.2°, 11.1°, and 18.9°; or
11.1°, 26.9°, and 28.1°; or
8.1°, 21.6°, and 26.9°; or
11.1°, 19.6°, and 26.9°; or
8.1°, 11.1°, and 19.6°.

In another general aspect, the crystalline form of compound of Formula (I) is characterized by X-ray powder diffraction pattern having peaks expressed in degrees 2θ±0.2° at 10.2°, 11.1°, and 21.6°; or
8.9°, 11.1°, and 21.6°; or
10.2°, 11.1°, and 18.9°; or
11.1°, 26.9°, and 28.1°; or
8.1°, 21.6°, and 26.9°; or
11.1°, 19.6°, and 26.9°; or
8.1°, 11.1°, and 19.6°; or
11.1°, 18.9° and 21.6°.

In another general aspect, there is provided a crystalline form of compound of Formula (I), characterized by X-ray powder diffraction pattern having at least two peaks expressed in degrees 2θ±0.2° selected from 10.2°, 11.1°, 14.6°, 18.9°, 19.6°, 21.6°, 27.0° and 28.1°.

In another aspect, the crystalline form of compound of Formula (I) is characterized by X-ray powder diffraction pattern having at least three peaks expressed in degrees 2θ±0.2° selected from 10.2°, 11.1°, 14.6°, 18.9°, 19.6°, 21.6°, 27.0° and 28.1°.

In another aspect, the crystalline form of compound of Formula (I) is characterized by X-ray powder diffraction pattern having at least four peaks expressed in degrees 2θ±0.2° selected from 10.2°, 11.1°, 14.6°, 18.9°, 19.6°, 21.6°, 27.0° and 28.1°.

In another aspect, the crystalline form of compound of Formula (I) is characterized by X-ray powder diffraction pattern having at least five peaks expressed in degrees 2θ±0.2° selected from 10.2°, 11.1°, 14.6°, 18.9°, 19.6°, 21.6°, 27.0° and 28.1°.

In another general aspect, the crystalline form of compound of Formula (I) is characterized by X-ray powder diffraction pattern having peaks expressed in degrees 2θ±0.2° at 10.2°, 11.1°, 18.9°, 19.6°, 21.6° and 28.1°.

In another general aspect, there is provided a crystalline form of compound of Formula (I) characterized by X-ray powder diffraction pattern having peaks expressed in degrees 2010.2° at 10.2°, 11.1°, 14.6°, 18.9°, 19.6°, 21.6°, 27.0° and 28.1°.

In another general aspect, there is provided a stable crystalline form of compound of Formula (I), characterized by X-ray powder diffraction pattern having at least two peaks expressed in degrees 2θ±0.2° selected from 10.2°, 11.1°, 14.6°, 18.9°, 19.6°, 21.6°, 27.0° and 28.1°, wherein the crystalline form remains stable for more than 1 month when stored at:

(i) 25°±2° C. and 60%±5% relative humidity, or
(ii) 30°±2° C. and 65%±5% relative humidity, or
(iii) 40°±2° C. and 75%±5% relative humidity.

In another general aspect, there is provided a non-hygroscopic crystalline form of compound of Formula (I) characterized by X-ray powder diffraction pattern having at least two peaks expressed in degrees 2θ±0.2° selected from 10.2°, 11.1°, 14.6°, 18.9°, 19.6°, 21.6°, 27.0° and 28.1°.

In another general aspect, there is provided a crystalline form of compound of Formula (I) characterized by X-ray powder diffraction pattern having peaks expressed in degrees 2θ±0.2° at 8.1°, 9.0°, 10.2°, 11.1°, 14.6°, 18.9°, 19.6°, 21.6°, 27.0° and 28.1°.

In another aspect, there is provided a crystalline form of compound of Formula (I) characterized by X-ray powder diffraction pattern having peaks expressed in degrees 2θ±0.2° at 8.1°, 9.0°, 10.2°, 11.1°, 14.6°, 18.9°, 19.6°, 21.6°, 27.0° and 28.1°, wherein the peak expressed in degrees 2θ at 10.2° (±0.2° is having at least about 25% relative intensity.

In another aspect, there is provided a crystalline form of compound of Formula (I) characterized by X-ray powder diffraction pattern having peaks expressed in degrees 2θ±0.2° at 8.1°, 9.0°, 10.2°. 11.1°, 14.6°, 18.9°, 19.6°, 21.6°, 27.0° and 28.1°, wherein the peak expressed in degrees 2θ at 10.2° (±0.2° is having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95, or at least 100% relative intensity.

In another general aspect, there is provided a crystalline form of compound of Formula (I) characterized by X-ray powder diffraction pattern having peaks expressed in degrees 2θ±0.2° at 8.1°. 9.0°, 10.2°. 10.7°. 11.1°. 14.6°, 16.2°. 17.2°, 17.4°. 18.9°, 19.6°. 21.2°, 21.6°. 22.5°, 22.7°, 23.1°. 25.7°, 26.5, 27.0°. 28.1° and 28.3°.

In another general aspect, there is provided a crystalline form of compound of Formula (I) characterized by X-ray powder diffraction pattern having peaks expressed in degrees 2010.2° at 8.1°. 9.0°, 10.2°, 10.7°, 11.1°, 14.6°, 16.2°, 17.2°, 17.4°, 18.9°. 19.6°. 21.2°, 21.6°, 22.45°, 22.7°, 23.1°. 25.7°, 26.5, 27.0°, 28.1° and 28.3°, wherein the peak expressed in degrees 2θ at 10.2° (±0.2° is having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95, or at least 100% relative intensity.

In another general aspect, there is provided a crystalline form of compound of Formula (I) characterized by X-ray powder diffraction pattern having peaks expressed in degrees 2θ±0.2° at 10.2°. 11.1°, 14.6°. 18.9°, 19.6°, 21.6°, 27.0° and 28.1°, wherein the peaks at 11.1° and 27.0° (±0.2° exhibit at least about 35% intensity relative to the intensity of the peak at 10.2° (±0.2°.

In another general aspect, there is provided a crystalline form of compound of Formula (I) characterized by X-ray powder diffraction pattern having peaks expressed in degrees 2θ±0.2° at 8.1°, 9.0°, 10.2°. 11.1°, 14.6°, 18.9°, 19.6°, 21.6°, 27.0° and 28.1°, wherein the peaks at 11.1° and 27.0° (±0.2° exhibit at least about 35% intensity relative to the intensity of the peak at 10.2° (±0.2°.

In another aspect, there is provided a crystalline form of compound of Formula (I) characterized by X-ray powder diffraction pattern having peaks expressed in degrees 2θ±0.2° at 8.1°, 9.0°, 10.2°, 11.1°, 14.6°, 18.9°, 19.6°, 21.6°, 27.0° and 28.1°, wherein the peaks at 11.1° and 27.0° (±0.2° exhibit at least about 50% intensity relative to the intensity of the peak at 10.2° (±0.2°.

In general, the crystalline form of compound of Formula (I) is characterized by X-ray powder diffraction pattern substantially as same as depicted in FIG. 1.

In general, the crystalline form of compound of Formula (I) is characterized by X-ray powder diffraction pattern substantially as same as depicted in FIG. 2.

In another general aspect, there is provided a process for the preparation of a crystalline form of compound of Formula (I), the process comprising:

(a) obtaining a solution of the compound of Formula (I) in a solvent mixture comprising halogenated solvent and a polar solvent; and (b) removing the solvent from the solution to obtain the crystalline form of the compound of Formula (I).

In one general aspect, the crystalline form of the compound of Formula (I) obtained by above process is characterized by X-ray powder diffraction pattern having at least two peaks expressed in degrees 2θ±0.2° selected from 10.2°, 11.1°, 14.6°, 18.9°, 19.6°, 21.6°, 27.0° and 28.1°.

In another aspect, the crystalline form of the compound of Formula (I) obtained by above process is characterized by X-ray powder diffraction pattern having peaks expressed in degrees 2θ±0.2° at 10.2°, 11.1°, 14.6°, 18.9°, 19.6°, 21.6°, 27.0° and 28.1°.

In general, the halogenated solvent at step (a), is selected from a group comprising methylene dichloride, ethylene dichloride, chloroform, and carbon tetrachloride, or mixtures thereof. Particularly, the halogenated solvent is methylene dichloride.

In general, the polar solvent at step (a) comprises of one or more of alcohols, ketones, esters and ethers.

In general, the alcohol is selected from a group comprising methanol, ethanol, propan-2-ol, butanol, pentanol, ethylene glycol, propylene glycol and glycerol, or mixtures thereof.

In general, the ketone is selected from a group comprising acetone, methyl ethyl ketone, methyl isobutyl ketone, methyl amyl ketone, cyclohexanone and diisobutyl ketone, or mixtures thereof.

In general, the ester is selected from a group comprising methyl acetate, ethyl acetate, isopropyl acetate, n-butyl acetate, sec-butyl acetate, tert-butyl acetate, isobutyl acetate, isoamyl acetate and hexyl acetate, or mixtures thereof.

In general, the ether is selected from a group comprising tetrahydrofuran, 2-methyltetrahydrofuran, 1,4 dioxane, diisopropyl ether, methyl tert-butyl ether and morpholine, or mixtures thereof.

Particularly, the solvent mixture at step (a) is a mixture of halogenated solvent and alcohol solvent.

More particularly, the halogenated solvent at step (a) is methylene dichloride and the polar solvent is methanol.

In another aspect, the solvent mixture at step (a) is a mixture of halogenated solvent and alcohol solvent, wherein the ratio of halogenated solvent to alcohol solvent is 1:10 v/v to 10:1 v/v. In another aspect, the ratio of halogenated solvent to alcohol solvent is 3:1 v/v to 1:1 v/v. In yet another aspect, the ratio of halogenated solvent to alcohol solvent is 2:1 v/v. In still yet another aspect, the ratio of halogenated solvent to alcohol solvent is 1:1 v/v.

In another aspect, the solvent mixture at step (a) is a mixture of methylene dichloride and methanol, wherein the ratio of methylene dichloride to methanol is 1:10 to 10:1 v/v. In another aspect, the ratio of methylene dichloride to methanol is 3:1 to 1:1 v/v. In yet another aspect, the ratio of methylene dichloride to methanol is 2:1 v/v. In still yet another aspect, the ratio of methylene dichloride to methanol is 1:1 v/v.

In general, the solution of the compound of Formula (I) can be obtained by preparing the solution of compound of Formula (I) in a solvent mixture comprising halogenated solvent and a polar solvent as per step (a) at room temperature or the reaction mixture comprising the compound of Formula (I) and the solvent mixture can be heated to a suitable temperature to obtain the solution of compound of Formula (I).

In general, the removal of solvent at step (b), comprises removal of halogenated solvent. The removal of halogenated solvent can be carried out by distillation, evaporation, evaporation under reduced pressure or evaporation under vacuum.

Particularly, as per step (b), first the removal of halogenated solvent is carried out to obtain a suspension and then the remaining solvent is removed to obtain the crystalline form of compound of Formula (I). The remaining solvent can be removed by distillation, evaporation, evaporation under reduced pressure or evaporation under vacuum, filtration, centrifugation or decantation.

Particularly, the solvent from the suspension can be removed by filtration, centrifugation or decantation. The obtained crystalline form of the compound of Formula (I) can be further dried.

In another general aspect, there is provided a process for the preparation of crystalline form of compound of Formula (I), the process comprising:

(a) treating the compound of Formula (I) in a solvent mixture comprising halogenated solvent and a polar solvent to obtain a reaction mixture; and (b) removing the halogenated solvent from the reaction mixture to obtain the crystalline form of compound of Formula (I).

In another general aspect, there is provided a process for the preparation of a crystalline form of compound of Formula (I), the process comprising:

(a) treating the compound of Formula (I) in a solvent mixture comprising halogenated solvent and a polar solvent to obtain a reaction mixture; and (b) removing the halogenated solvent from the reaction mixture to obtain the crystalline form of compound of Formula (I), wherein the crystalline form of compound of Formula (I) is characterized by X-ray powder diffraction pattern having at least two peaks expressed in degrees 2θ±0.2° selected from 10.2°, 11.1°, 14.6°, 18.9°, 19.6°, 21.6°, 27.0° and 28.1°.

In another aspect, the obtained crystalline form of compound of Formula (I) is characterized by X-ray powder diffraction pattern having peaks expressed in degrees 2θ±0.2° at 10.2°, 11.1°, 14.6°, 18.9°, 19.6°, 21.6°, 27.0° and 28.1°.

In another general aspect, there is provided a process for the preparation of crystalline form of compound of Formula (I), the process comprising:

(a) treating the compound of Formula (I) in a solvent mixture comprising of halogenated solvent and a polar solvent to obtain a first reaction mixture;

(b) removing the halogenated solvent from the first reaction mixture by distillation to obtain a second reaction mixture; and (c) obtaining the crystalline compound of Formula (I) from the second reaction mixture followed by drying at 60-80° C.

In another general aspect, there is provided a process for the preparation of a crystalline form of compound of Formula (I), the process comprising:

(a) treating the compound of Formula (I) in a solvent mixture comprising of halogenated solvent and a polar solvent to obtain a first reaction mixture;

(b) removing the halogenated solvent from the first reaction mixture by distillation to obtain a second reaction mixture; and (c) obtaining the crystalline compound of Formula (I) from second reaction mixture followed by drying at 60-80° C.;

wherein the crystalline form of compound of Formula (I) is characterized by X-ray powder diffraction pattern having at least two peaks expressed in degrees 2θ±0.2° selected from 10.2°, 11.1°, 14.6°, 18.9°, 19.6°, 21.6°, 27.0° and 28.1°.

In another aspect, the obtained crystalline form of compound of Formula (I) is characterized by X-ray powder diffraction pattern having peaks expressed in degrees 2θ±0.2° at 10.2°, 11.1°, 14.6°, 18.9°, 19.6°, 21.6°, 27.0° and 28.1°.

In general, the halogenated solvent at step (a), is selected from a group comprising methylene dichloride, ethylene dichloride, chloroform, and carbon tetrachloride, or mixtures thereof. Particularly, the halogenated solvent is methylene dichloride.

In general, the polar solvent at step (a) comprises of one or more of alcohols, ketones, esters and ethers.

In general, the alcohol is selected from a group comprising methanol, ethanol, propan-2-ol, butanol, pentanol, cetyl alcohol, ethylene glycol, propylene glycol and glycerol, or mixtures thereof.

In general, the ketone is selected from a group comprising acetone, methyl ethyl ketone, methyl isobutyl ketone, methyl amyl ketone, cyclohexanone and diisobutyl ketone or mixtures thereof.

In general, the ester is selected from a group comprising methyl acetate, ethyl acetate, isopropyl acetate, n-butyl acetate, sec-butyl acetate, tert-butyl acetate, isobutyl acetate, isoamyl acetate and hexyl acetate, or mixtures thereof.

In general, the ether is selected from a group comprising tetrahydrofuran, 2-methyltetrahydrofuran, 1,4 dioxane, diisopropyl ether, methyl tert-butyl ether and morpholine, or mixtures thereof.

In general, the removal of halogenated solvent in step (b) is carried out by distillation, evaporation or centrifugation.

Particularly, the removal of halogenated solvent in step (b) is carried out by distillation, evaporation, evaporation under reduced pressure or evaporation under vacuum.

Particularly, the solvent at step (a) is a mixture of halogenated solvent and alcohol solvent.

More Particularly, the halogenated solvent at step (a) is methylene dichloride and the polar solvent is methanol.

In another general aspect, there is provided a process for the preparation of a crystalline form of compound of Formula (I), the process comprising:

(a) treating the compound of Formula (I) with a base in alcohol solvent in the presence of water to obtain a first reaction mixture;

(b) adding an acid to the first reaction mixture to obtain a second reaction mixture; and (c) stirring the second reaction mixture to obtain the crystalline form of the compound of Formula (I);

wherein the crystalline form of the compound of Formula (I) is characterized by X-ray powder diffraction pattern having peaks expressed in degrees 2θ±0.2° at 8.1°, 9.0°, 10.2°, 11.1°, 14.6°, 18.9°, 19.6°, 21.6°, 27.0° and 28.1°.

In general, the base at step (a), can be selected from sodium hydroxide, potassium hydroxide, sodium carbonate, lithium hydroxide, calcium hydroxide, magnesium hydroxide, lithium carbonate, potassium carbonate, cesium carbonate, sodium bicarbonate, and potassium bicarbonate, or mixtures thereof. In particular, the base is sodium hydroxide.

In general, the alcohol solvent at step (a), can be selected from methanol, ethanol, propan-2-ol, butanol, pentanol, ethylene glycol, propylene glycol and glycerol, or mixtures thereof. In particular, the alcohol solvent is methanol.

In general, the acid at step (b), can be selected from hydrochloric acid, sulphuric acid, phosphoric acid, hydrobromic acid and nitric acid. In particular, the acid is hydrochloric acid.

In another general aspect, there is provided a composition comprising the crystalline form of compound of Formula (I).

In another general aspect, there is provided a pharmaceutical composition comprising crystalline form of compound of Formula (I) and pharmaceutically acceptable excipient, diluents or carriers.

In another general aspect, there is provided a pharmaceutical composition comprising crystalline form of compound of Formula (I) useful in the treatment of conditions associated with anemia.

In particular, pharmaceutical composition includes the crystalline form of compound of Formula (I) with pharmaceutically acceptable carrier.

In another general aspect, there is provided a pharmaceutical composition comprising a crystalline form of compound of Formula (I) and pharmaceutically acceptable carrier, diluents and excipients; wherein the crystalline form is characterized by X-ray powder diffraction pattern having at least two peaks expressed in degrees 2θ±0.2° selected from 10.2°, 11.1°, 14.6°, 18.9°, 19.6°, 21.6°, 27.0° and 28.1°.

In another aspect, there is provided a pharmaceutical composition comprising a crystalline form of compound of Formula (I) and pharmaceutically acceptable carrier, diluents and excipients; wherein the crystalline form is characterized by X-ray powder diffraction pattern having peaks expressed in degrees 2θ±0.2° at 10.2°, 11.1°, 14.6°, 18.9°, 19.6°, 21.6°, 27.0° and 28.1°.

In another general aspect, there is provided a pharmaceutical composition comprising a crystalline form of compound of Formula (I) and pharmaceutically acceptable carrier, diluents and excipients; wherein the crystalline form is characterized by X-ray powder diffraction pattern having peaks expressed in degrees 2θ±0.2° at 8.1°, 9.0°, 10.2°, 11.1°, 14.6°, 18.9°, 19.6°, 21.6°, 27.0° and 28.1°.

In another general aspect, there is provided a pharmaceutical composition comprising crystalline form of compound of Formula (I) useful in the treatment of conditions associated with anemia, wherein the crystalline form is characterized by X-ray powder diffraction pattern having at least two peaks expressed in degrees 2θ±0.2° selected from 10.2°, 11.1°, 14.6°, 18.9°, 19.6°, 21.6°, 27.0° and 28.1°.

In another general aspect, there is provided a pharmaceutical composition comprising crystalline form of compound of Formula (I) useful in the treatment of conditions associated with anemia, wherein the crystalline form is characterized by X-ray powder diffraction pattern having peaks expressed in degrees 2θ±0.2° at 10.2°, 11.1°, 14.6°, 18.9°, 19.6°, 21.6°, 27.0° and 28.1°.

In another general aspect, there is provided a method of treatment of anemia in a patient comprising administering to a patient in need thereof a pharmaceutical composition comprising a crystalline form of compound of Formula (I) and pharmaceutically acceptable carrier, diluents and excipients, wherein the crystalline form is characterized by X-ray powder diffraction pattern having peaks expressed in degrees 2θ±0.2° at 10.2°, 11.1°, 14.6°, 18.9°, 19.6°, 21.6°, 27.0° and 28.1°.

In another general aspect, there is provided a pharmaceutical composition comprising crystalline form of compound of Formula (I) useful in the treatment of conditions associated with anemia, wherein the crystalline form is characterized by X-ray powder diffraction pattern having peaks expressed in degrees 2θ±0.2° at 8.1°, 9.0°, 10.2°, 11.1°, 14.6°, 18.9°, 19.6°, 21.6°, 27.0° and 28.1°.

In another general aspect, there is provided a method of treatment of anemia in a patient comprising administering to a patient in need thereof a pharmaceutical composition comprising a crystalline form of compound of Formula (I) and pharmaceutically acceptable carrier, diluents and excipients, wherein the crystalline form is characterized by X-ray powder diffraction pattern having peaks expressed in degrees 2θ±0.2° at 8.1°, 9.0°, 10.2°, 11.1°, 14.6°, 18.9°, 19.6°, 21.6°, 27.0° and 28.1°.

Pharmaceutically acceptable carriers, adjuvants or vehicles that may be used in the pharmaceutical compositions of this invention include, but are not limited to, microcrystalline cellulose, croscarmellose sodium, kollidon 30 powder (polyvinylpyrrolidone, povidone), colloidal silicon dioxide M5-P, magnesium stearate, microcrystalline cellulose, sodium lauryl sulfate, hydroxy propyl methyl cellulose and colloidal silicon dioxide M5-P.

Process

In another general aspect, there is provided a process for the preparation of a compound of Formula (I), (I)

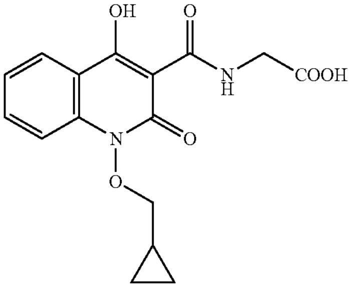

the process comprising:

(a) reacting a compound of Formula (VII), (VII)

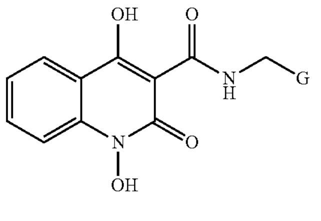

with a compound of Formula (VII), (VIII)

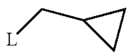

wherein,

L is a leaving group;

to obtain a compound of Formula (IX);

(IX)

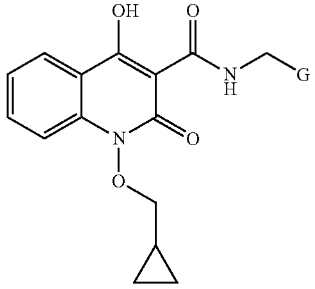

wherein,

G is selected from CN, —COORa and —CONRbRc;

Ra is selected from alkyl, cycloalkyl, heterocycloalkyl, aryl and heteroaryl; wherein Ra is optionally further substituted with one or more of chloro, bromo, iodo, cyano, hydroxy, nitro, amino, alkylamino, carbonyl, aminocarbonyl, thio, alkylthio, alkyl, cycloalkyl, heterocycloalkyl, aryl or heteroaryl; and Rb and Rc each independently is hydrogen or Ra;

and, (b) converting the compound of Formula (IX) to the compound of Formula (I).

In general, the leaving group L in the compound of Formula (VIII) is selected from halogens, sulfonate esters and perfluoroalkylsulfonates. In Particular, the halogen is selected from chloro, bromo, iodo or fluoro; sulfonate ester is selected from mesylate, tosylate, nosylate, benzene sulfonate, ethyl mesylate and sec-butyl tosylate; and perfluoroalkylsulfonates is triflate.

Particularly, the leaving group L in the compound of Formula (VIII) is chloro, bromo, mesylate, tosylate, nosylate or benzene sulfonate; more particularly, the leaving group L in the compound of Formula (VIII) is chloro, bromo or tosylate.

In one general aspect, G in the compound of Formula (VII) and (IX) is —CN or —COORa, wherein Ra is $C_{1-4}$ alkyl.

In another general aspect, G in the compound of Formula (VII) and (IX) is —CN or —COORa, wherein Ra is methyl or ethyl.

In general, the step (a) is carried out in presence of a base in one or more solvents.

The base for the purpose may be selected from organic bases comprising triethylamine, diisopropylethylamine, piperidine, 4-dimethylaminopyridine (DMAP), 1,8-diazabicyclo[5.4.0]undec-7-ene (DBU), 1,5-diazabicyclo[4.3.0]non-5-ene (DBN), 1,4-diazabicyclo[2.2.2]octane (DABCO), N-methylmorpholine, N-methyl pyrrolidine, or mixtures thereof; or inorganic bases comprising potassium hydroxide, sodium hydroxide, lithium hydroxide, calcium hydroxide, magnesium hydroxide, sodium carbonate, lithium carbonate, potassium carbonate, cesium carbonate, sodium bicarbonate, potassium bicarbonate, sodium hydride, sodium methoxide, potassium methoxide, sodium tert-butoxide and potassium tert-butoxide, or mixtures thereof.

The solvent for the purpose may be selected from N,N-dimethylformamide (DMF), dimethylacetamide, dimethyl sulfoxide, tetrahydrofuran, ethyl acetate, acetonitrile, toluene, xylene, isopropyl acetate, 2-methyltetrahydrafuran, 1,4-dioxane, acetone, or mixtures thereof.

In general, the step (a) may be carried out at a temperature ranging from room temperature to reflux temperature of the solvent used. Particularly, the reaction may be carried at a temperature of 40° C. to 70° C., more particularly, at a temperature of 50° C. to 70° C. The reaction may be carried out for a time sufficient for the completion of reaction. After completion of the reaction, the compound of Formula (IX) may be isolated from the reaction mixture by any of the processes under common knowledge of a person skilled in the art like filtration or extraction.

In another general aspect, there is provided a compound of Formula (VII), (VII)

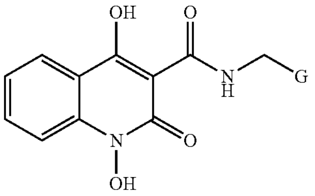

wherein,

G is selected from CN, —COORa and —CONRbRc,

Ra is selected from alkyl, cycloalkyl, heterocycloalkyl, aryl and heteroaryl; wherein Ra is optionally further substituted with one or more of chloro, bromo, iodo, cyano, hydroxy, nitro, amino, alkylamino, carbonyl, aminocarbonyl, thio, alkylthio, alkyl, cycloalkyl, heterocycloalkyl, aryl or heteroaryl; and Rb and Rc each independently is hydrogen or Ra.

In one general aspect, there is provided a compound of Formula (VII), wherein G is —CN or —COORa, wherein Ra is $C_{1-4}$alkyl.

In another general aspect, G in the compound of Formula (VII) is —CN or —COORa, wherein Ra is methyl or ethyl.

The compound of Formula (VII) is used as an intermediate for the synthesis of compound of Formula (I).

In another general aspect, there are provided novel intermediates for the synthesis of compound of Formula (I) selected from:

a compound of Formula (VIIa), compound of Formula (VIIb) and compound of Formula (IXa)

(VIIa)

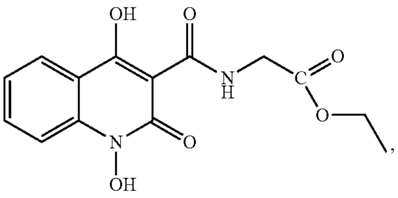

(VIIb)

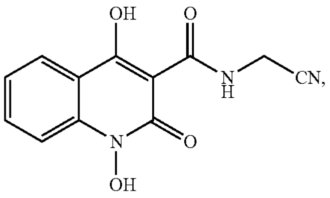

-continued (IXa)

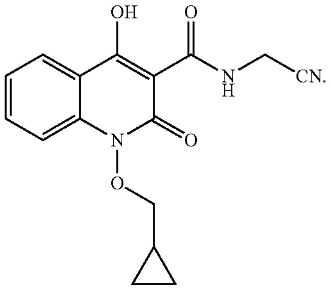

In another general aspect, there is provided a process for the preparation of a compound of (VII)

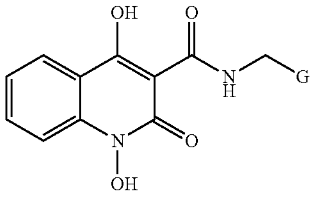

the process comprising:

(a) converting a compound of Formula (IV), (IV)

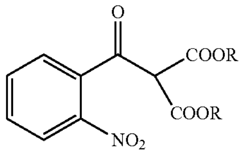

to a compound of Formula (VI), (VI)

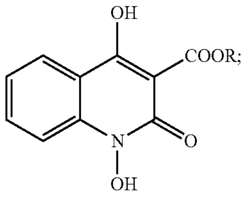

and, (b) reacting the compound of Formula (VI) with a compound of Formula (X)

(X)

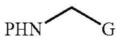

to obtain the compound of Formula (VII);

wherein, each R is independently selected from alkyl and aryl,

P is selected from hydrogen or amino protecting group;

G is selected from CN, —COORa and —CONRbRc

Ra is selected from alkyl, cycloalkyl, heterocycloalkyl, aryl and heteroaryl; wherein Ra is optionally further substituted with one or more of chloro, bromo, iodo, cyano, hydroxy, nitro, amino, alkylamino, carbonyl, aminocarbonyl, thio, alkylthio, alkyl, cycloalkyl, heterocycloalkyl, aryl or heteroaryl; and Rb and Rc each independently is hydrogen or Ra.

In general, the step (a) may be carried out by reacting the compound of Formula (IV) with zinc and alcoholic hydrochloric acid.

In general, the step (b) is carried out in presence of a base in one or more solvents.

In general, the base for the purpose may be selected from organic bases comprising triethylamine, diisopropylethylamine, piperidine, 4-dimethylaminopyridine (DMAP), 1,8-diazabicyclo[5.4.0]undec-7-ene (DBU), 1,5-diazabicyclo [4.3.0]non-5-ene (DBN), 1,4-diazabicyclo[2.2.2]octane (DABCO), N-methylmorpholine, N-methyl pyrrolidine, or mixtures thereof; or inorganic bases comprising potassium hydroxide, sodium hydroxide, lithium hydroxide, calcium hydroxide, magnesium hydroxide, sodium carbonate, lithium carbonate, potassium carbonate, cesium carbonate, sodium bicarbonate, potassium bicarbonate, sodium hydride, sodium methoxide, potassium methoxide, sodium tert-butoxide and potassium tert-butoxide, or mixtures thereof.

In general, the solvent for the purpose may be selected from N,N-dimethylformamide (DMF), dimethylacetamide, dimethyl sulfoxide, tetrahydrofuran, ethyl acetate, acetonitrile, toluene, xylene, isopropyl acetate, 2-methyltetrahydrafuran, 1,4-dioxane, acetone, or mixtures thereof.

In another general aspect, R in the compound of Formula (IV) and (VI) is $C_{1-4}$alkyl; P in the compound of Formula (X) is hydrogen and G in the compound of Formula (VII) and (X) s —CN or —COORa, wherein Ra is $C_{1-4}$ alkyl. In another general aspect, R in the compound of Formula (IV) and (VI) is methyl or ethyl; P in the compound of Formula (X) is hydrogen and G in the compound of Formula (VII) and (X) s-CN or —COORa, wherein Ra is methyl or ethyl.

In another general aspect, there is provided a process for the preparation of a compound of Formula (I), the process comprising:

(a) converting a compound of Formula (IV), (IV)

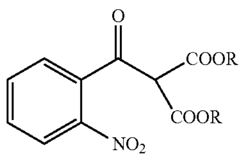

to a compound of Formula (VI);

(VI)

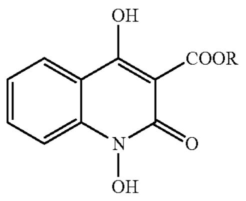

(b) reacting the compound of Formula (VI) with a compound of Formula (X), (X)

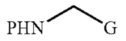

wherein,

P is selected from hydrogen or amino protecting group; to obtain a compound of Formula (VII);

(VII)

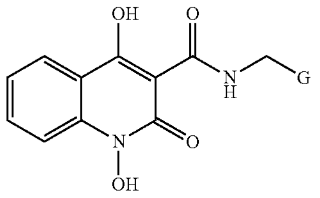

(c) reacting the compound of Formula (VII), (VII)

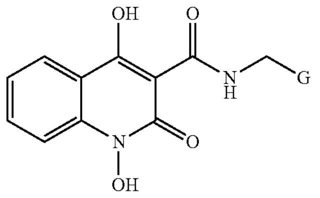

with a compound of Formula (VIII), (VIII)

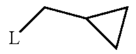

wherein,

L is a leaving group, to obtain a compound of Formula (IX);

(IX)

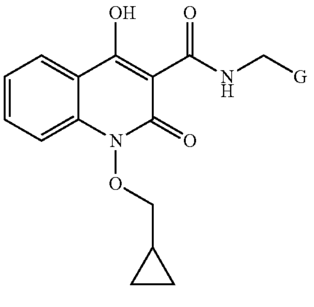

and, (d) converting the compound of Formula (IX) to the compound of Formula (I);

wherein, each R is independently selected from alkyl and aryl and

G is selected from CN, —COORa and —CONRbRc;

Ra is selected from alkyl, cycloalkyl, heterocycloalkyl, aryl and heteroaryl; wherein Ra is optionally further substituted with one or more of chloro, bromo, iodo, cyano, hydroxy, nitro, amino, alkylamino, carbonyl, aminocarbonyl, thio, alkylthio, alkyl, cycloalkyl, heterocycloalkyl, aryl or heteroaryl; and Rb and Rc is each independently is hydrogen or Ra.

In general, the leaving group L is selected from halogens, sulfonate esters and perfluoroalkylsulfonates. In Particular, the halogen is selected from chloro, bromo, iodo or fluoro; sulfonate ester is selected from mesylate, tosylate, nosylate, benzene sulfonate, ethyl mesylate and sec-butyl tosylate; and perfluoroalkylsulfonates is triflate.

The amino protecting group is selected from a group comprising-tert-butyloxycarbonyl (BOC), -carbobenzyloxy (Cbz or Z), -9-fluorenyl-methyloxycarbonyl (Fmoc), -benzyl (Bn), -p-methoxyphenyl (PMP), -acetyl (Ac) and -trifluororacetyl (TFA).

The compound of Formula (IV) can be converted to a compound of Formula (VI) by reacting the compound of Formula (IV) with zinc in alcoholic HCl to obtain a compound of Formula (V), which converts to the compound of Formula (VI).

(V)

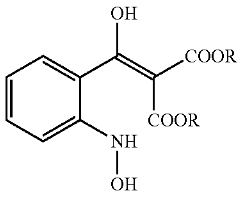

The compound of Formula (VI) can be converted to a compound of Formula (VII) in the presence of a base.

The compound of Formula (VII) can be converted to compound of Formula (IX) by reacting the compound of Formula (VII) with a compound of Formula (VIII) in the presence of a base.

The compound of Formula (IX) can be converted to compound of Formula (I) by the hydrolyzing the compound of Formula (IX) to compound of Formula (I) in the presence of acid or base.

The base can be selected from inorganic base or organic base, or any combination thereof. The inorganic base can be selected from a group comprising potassium hydroxide, sodium hydroxide, lithium hydroxide, calcium hydroxide, magnesium hydroxide, sodium carbonate, lithium carbonate, potassium carbonate, cesium carbonate, sodium bicarbonate, potassium bicarbonate, sodium hydride, sodium methoxide, potassium methoxide, sodium tert-butoxide and potassium tert-butoxide.

The organic base can be selected from a group comprising ammonia, methylamine, triethylamine, ethyl amine, diethylamine, methylethylamine, diisopropylethylamine, purine, pyridine, pyrimidine, piperidine, 4-dimethylaminopyridine (DMAP), 1,8-diazabicyclo[5.4.0]undec-7-ene(DBU), 1,5-diazabicyclo[4.3.0]non-5-ene (DBN) and 1,4-diazabicyclo[2.2.2]octane (DABCO).

The acid can be selected from group comprising hydrochloric acid, sulphuric acid, phosphoric acid, hydrobromic acid and nitric acid.

In another general aspect, there are provided compounds of Formulae A, B, C, D and E.

(A)

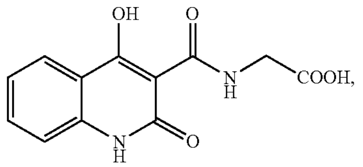

(B)

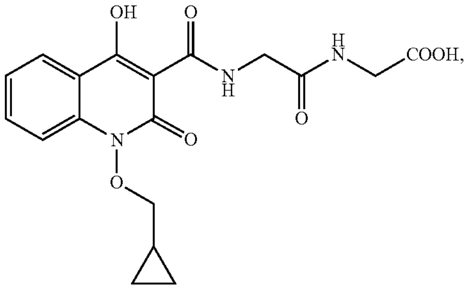

(C)

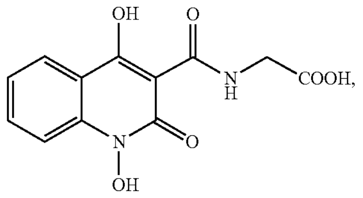

-continued (D)

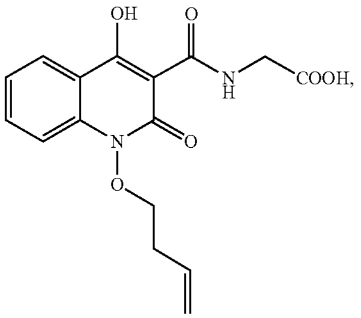

(E)

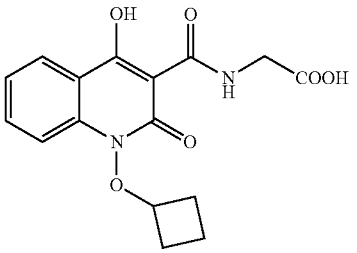

In another general aspect, there are provided compounds of Formulae D and E (D)

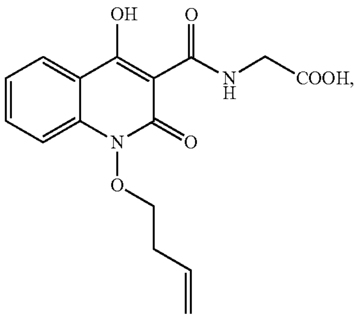

(E)

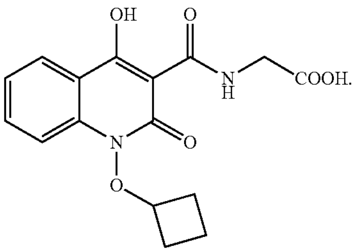

In another general aspect, there is provided a compound of Formula (I) free from compound of Formulae A, B, C, D or E.

In another general aspect, there is provided a compound of Formula (I) free from compound of Formulae D or E.

In another general aspect, there is provided a compound of Formula (I) having a purity of at least about 99% by area percentage of HPLC. In particular, compound of Formula (I) having a purity of at least about 99%, more particularly, a purity of at least about 99.5%, further more particularly, a purity of at least about 99.8%, most particularly, a purity of at least about 99.9% by area percentage of HPLC.

In another general aspect, there is provided a composition comprising compound of Formula (I) and one or more of compounds of Formulae A, B, C, D or E in an amount less than about 0.15% by area percentage of HPLC relative to the compound of Formula (I).

In another general aspect, there is provided a composition comprising a compound of Formula (I) and one or more of compounds of Formulae C, D or E in an amount less than about 0.15% by area percentage of HPLC relative to the compound of Formula (I).

In another general aspect, there is provided a composition comprising a compound of Formula (I) having a purity of about 99% or more and one or more of compounds of Formulae C, D or E in an amount less than about 0.15% by area percentage of HPLC relative to the compound of Formula (I).

In another general aspect, there is provided a composition comprising compound of Formula (I) and compound of Formula A in an amount less than about 0.15% by area percentage of HPLC relative to the compound of Formula (I).

In another general aspect, there is provided a composition comprising compound of Formula (I) and compound of Formula B in an amount less than about 0.15% by area percentage of HPLC relative to the compound of Formula (I).

In another general aspect, there is provided a composition comprising compound of Formula (I) and compound of Formula C in an amount less than about 0.15% by area percentage of HPLC relative to the compound of Formula (I).

In another general aspect, there is provided a composition-comprising compound of Formula (I) and compound of Formula D in an amount less than about 0.15% by area percentage of HPLC relative to the compound of Formula (I).

In another general aspect, there is provided a composition comprising a compound of Formula (I) having a purity of about 99% or more and a compound of Formula D in an amount less than about 0.15% by area percentage of HPLC relative to the compound of Formula (I).

In another general aspect, there is provided a composition comprising compound of Formula (I) and compound of Formula E in an amount less than about 0.15% by area percentage of HPLC relative to the compound of Formula (I).

In another general aspect, there is provided a composition comprising a compound of Formula (I) having a purity of about 99% or more and a compound of Formula D in an amount less than about 0.15% by area percentage of HPLC relative to the compound of Formula (I).

In another general aspect, there is provided a high purity compound of Formula (I), wherein the high purity is characterized by a purity of greater than 99% or more, by area percentage by HPLC and one or more of the following:

(i) less than about 0.15% compound of Formula C as an impurity; or (ii) less than about 0.15% compound of Formula D as an impurity; or (iii) less than about 0.15% compound of Formula E as an impurity.

In another general aspect, there is provided a composition comprising a crystalline form of compound of Formula (I) having a purity of about 99% or more and one or more of compounds of Formulae A, B, C, D or E in an amount less than about 0.15% by area percentage of HPLC relative to the compound of Formula (I), wherein the crystalline form of compound of Formula (I) is characterized by X-ray powder diffraction pattern having at least two peaks expressed in degrees 2θ±0.2° selected from 10.2°, 11.1°. 14.6°, 18.9°, 19.6°, 21.6°, 27.0° and 28.1°.

In another aspect, there is provided a composition comprising a crystalline form of compound of Formula (I) having a purity of about 99% or more and one or more of compounds of Formulae A, B, C, D or E in an amount less than about 0.15% by area percentage of HPLC relative to the compound of Formula (I), wherein the crystalline form of compound of Formula (I) is characterized by X-ray powder diffraction pattern having peaks expressed in degrees 2θ±0.2° at 10.2°, 11.1°, 14.6°. 18.9°, 19.6°, 21.6°, 27.0° and 28.1°.

In another aspect, there is provided a composition comprising a crystalline form of compound of Formula (I) having a purity of about 99% or more and one or more of compounds of Formulae C, D or E in an amount less than about 0.15% by area percentage of HPLC relative to the compound of Formula (I), wherein the crystalline form of compound of Formula I is characterized by X-ray powder diffraction pattern having at least two peaks expressed in degrees 2θ±0.2° selected from 10.2°, 11.1°. 14.6°, 18.9°, 19.6°. 21.6°. 27.0° and 28.1°.

In another aspect, there is provided a composition comprising a crystalline form of compound of Formula (I) having a purity of about 99% or more and one or more of compounds of Formulae C, D or E in an amount less than about 0.15% by area percentage of HPLC relative to the compound of Formula (I), wherein the crystalline form of compound of Formula (I) is characterized by X-ray powder diffraction pattern having peaks expressed in degrees 2θ±0.2° at 10.2°. 11.1°, 14.6°, 18.9°, 19.6°, 21.6°, 27.0° and 28.1°.

In another aspect, there is provided a composition comprising a crystalline form of compound of Formula (I) having a purity of about 99% or more and compound of Formula D in an amount less than about 0.15% by area percentage of HPLC relative to the compound of Formula (I), wherein the crystalline form of compound of Formula (I) is characterized by X-ray powder diffraction pattern having at least two peaks expressed in degrees 2θ±0.2° selected from 10.2°, 11.1°, 14.6°, 18.9°. 19.6°, 21.6°. 27.0° and 28.1°.

In another aspect, there is provided a composition comprising a crystalline form of compound of Formula (I) having a purity of about 99% or more and compound of Formula D in an amount less than about 0.15% by area percentage of HPLC relative to the compound of Formula (I), wherein the crystalline form of compound of Formula (I) is characterized by X-ray powder diffraction pattern having peaks expressed in degrees 2θ±0.2° at 10.2°, 11.1°, 14.6°. 18.9°, 19.6°, 21.6°, 27.0° and 28.1°.

In another aspect, there is provided a composition comprising a crystalline form of compound of Formula (I) having a purity of about 99% or more and compound of Formula E in an amount less than about 0.15% by area percentage of HPLC relative to the compound of Formula (I), wherein the crystalline form of compound of Formula (I) is characterized by X-ray powder diffraction pattern having at least two peaks expressed in degrees 2θ±0.2° selected from 10.2°, 11.1°, 14.6°, 18.9°, 19.6°, 21.6°, 27.0° and 28.1°.

In another aspect, there is provided a composition comprising a crystalline form of compound of Formula (I) having a purity of about 99% or more and compound of Formula E in an amount less than about 0.15% by area percentage of HPLC relative to the compound of Formula (I), wherein the crystalline form of compound of Formula (I) is characterized by X-ray powder diffraction pattern having peaks expressed in degrees 2θ±0.2° at 10.2°, 11.1°, 14.6°, 18.9°, 19.6°, 21.6°, 27.0° and 28.1°.

In another general aspect, there is provided a high purity crystalline form of compound of Formula (I), wherein the high purity is characterized by a purity of greater than 99% or more, by area percentage by HPLC and one or more of the following:

(i) less than about 0.15% compound of Formula A as an impurity; or (ii) less than about 0.15% compound of Formula B as an impurity; or (iii) less than about 0.15% compound of Formula C as an impurity; or (iii) less than about 0.15% compound of Formula D as an impurity; or (iii) less than about 0.15% compound of Formula E as an impurity;

wherein the crystalline form of compound of Formula (I) is characterized by X-ray powder diffraction pattern having at least two peaks expressed in degrees 2θ±0.2° selected from 10.2°, 11.1°, 14.6°, 18.9°, 19.6°, 21.6°, 27.0° and 28.1°.

In another general aspect, there is provided a process for the preparation of compound of Formula (I) as depicted in Scheme-1.

Scheme-1

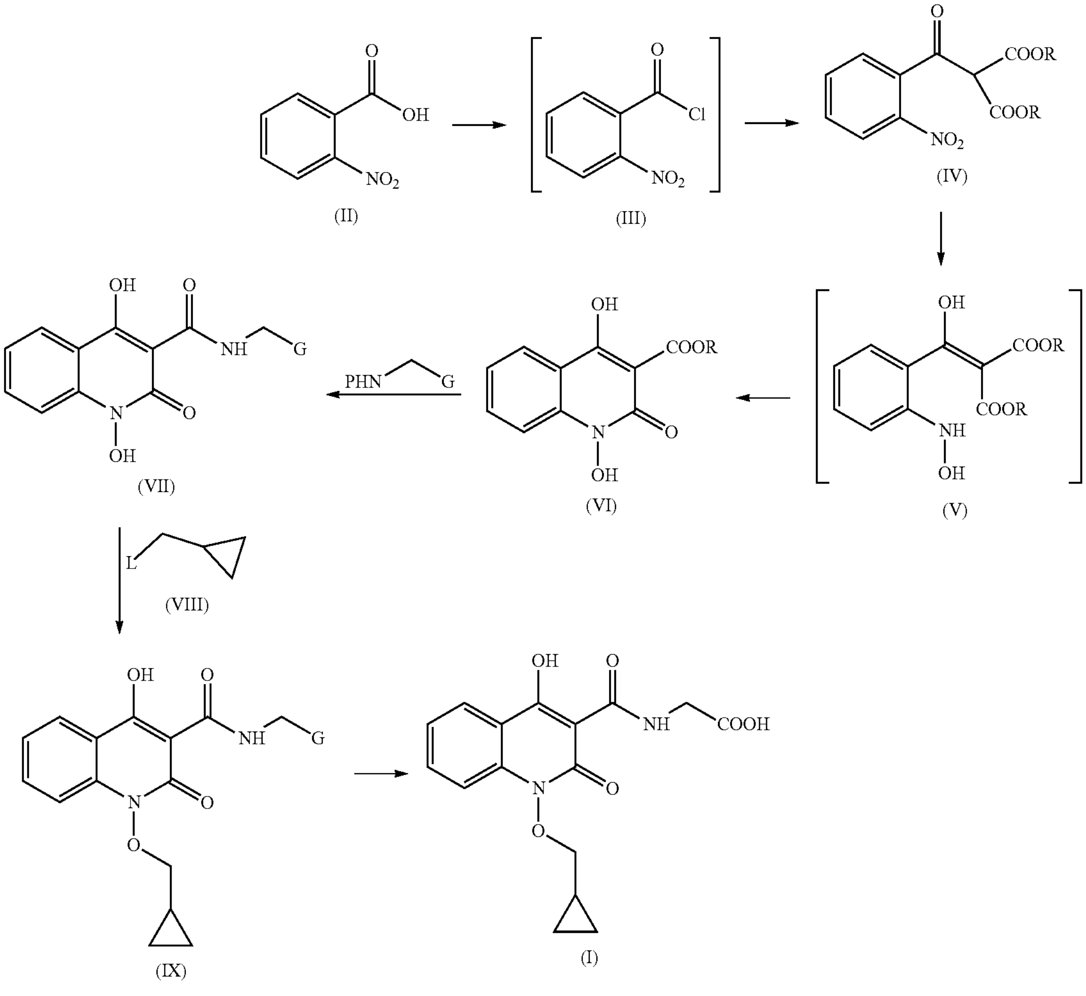

(II) (III) (IV) (V) (VI) (VII) (VIII) (IX) (I)

Analytical Methods

The crystalline form of compound of Formula (I) is characterized by X-ray powder diffraction (XRPD) pattern. In particular, the solid form of compound of Formula (I) is characterized by X-ray powder diffraction pattern obtained using $CuK\alpha_1$ radiation on a PANalytical X'Pert Pro or equivalent X-ray powder diffraction instrument.

The relative intensities of the various peaks reported and figures herein may vary due to a number of factors such as orientation effects of crystals in the X-ray beam or the purity of the material being analyzed or the degree of crystallinity of the sample. The powder X-ray diffraction pattern peak positions may also shift due to variations in sample height but the peak positions will remain almost the same as defined in the figure. A skilled person in the field of crystallography will also appreciate that measurements using a different wavelength will result in different shifts according to the Bragg equation $n\lambda=2d \sin \theta$. The powder X-ray diffraction patterns generated by use of alternative wavelengths are considered to be alternative representations of the powder X-ray diffraction patterns of the crystalline materials of the present invention and as such are within the scope of the present invention.

Particularly, the X-ray powder diffraction spectrum was measured under the following experimental conditions:

Instrument: X-Ray Diffractometer, PW3050/60, Make: PANalytical.

X-Ray: Cu K alpha radiation

Tension: 45 KV

Current: 40 mA

Divergence slit: Automatic

Incident Beam Side

Off set: 0.000

Anti-scatter slit: ½°

Receiving slit: None

Detector: PIXcel1D-Medipix3

Mode: Scanning line detector (1D)

Method Parameter

Start position: 2° 2θ

End position: 40° 2θ

Step size: 0.02° rad

Time per step: 67.575s

Scan mode: Continuous

The HPLC purity of the compound of Formula (I) was calculated using following method: Instrument Name: Waters Alliance e2695 HPLC system or equivalent

| HPLC CHROMATOGRAPHIC CONDITIONS: | |
|---|---|
| Column: | Zorbax SB-Phenyl (150 mm × 4.6 mm, 5 μm) Ghost hunter column (4.6 mm × 53 mm, Part No.: 0646PRONTOGHO, Make: Prontosil) or equivalent |
| Detector | UV-VIS or PDA detector |
| Flow rate | 2.0 mL/min |
| Wavelength | 230 nm |
| Injection volume | 10 μL |
| Column temperature | 30° C. |
| Run time | 70 minutes |
| Sample cooler temperature | 25° C. |

| Gradient composition: | | |
|---|---|---|
| Time (minutes) | % Mobile phase A | % Mobile phase B |
| 0 | 82 | 18 |
| 18 | 82 | 18 |
| 40 | 40 | 60 |
| 50 | 30 | 70 |
| 60 | 30 | 70 |
| 63 | 82 | 18 |
| 70 | 82 | 18 |

Preparation of Dilute Orthophosphoric Acid Solution:

10 mL of Orthophosphoric acid was transferred into 100 mL volumetric flask and the volume was make up to the mark with Milli-Q water and mixed well.

Preparation of Buffer:

1.36 g of potassium dihydrogen phosphate was transferred in to suitable container. About 1000 mL of Milli Q water was added and sonicated to dissolve the content and mixed well. The pH 3.5±0.05 was adjusted with controlled addition of dilute Orthophosphoric acid solution and filtered through 0.45 μm PVDF membrane filter paper.

Mobile Phase-A:

Degassed mixture of Buffer: Methanol in the volume ratio of 95:05 (v/v).

Mobile Phase-B:

Degassed mixture of Acetonitrile: Buffer in the volume ratio of 70:30 (v/v).

Diluent:

Degassed mixture of Acetonitrile: Methanol in the volume ratio of 50:50 (v/v)

Blank: Diluent as a Blank.

The $^{1}H$ NMR was recorded on Bruker AVANCE Neo at 400 MHz using DMSO-$d_6$ solvent.

The general aspects of the invention can further be illustrated by following examples.

EXAMPLES

Example-1: Preparation of Crystalline Form of Compound of Formula (I)

In a 500 mL round bottom flask, compound of Formula (I) (10 g) was added to a mixture of methanol (40 mL) and methylene dichloride (80 mL) at 25-35° C. The temperature of the reaction mixture was raised to 40-60° C. and then methylene dichloride was distilled off from the reaction mixture up to 60° C. atmospherically. The reaction mass was cooled to 25-35° C. and stirred for 1-2 hours. The reaction mass was then filtered under suction. Wet cake was then dried at 70-75° C. for 3-4 hours to obtain crystalline compound.

HPLC purity: 99.9%; Content of compound of Formula A: Not detected;

Content of compound of Formula B: Not detected;

Content of compound of Formula C: Not detected;

Content of compound of Formula D: 0.04%.

Polymorphic Data (XRPD):

The X-ray powder diffraction pattern is depicted in FIG. 1.

| 2θ | Relative Intensity |
|---|---|
| 10.2° ± 0.2° | 95.6% |
| 11.1° ± 0.2° | 96.9% |
| 14.6° ± 0.2° | 63.0% |
| 18.9° ± 0.2° | 48.1% |
| 19.6° ± 0.2° | 31.0% |
| 21.6° ± 0.2° | 88.0% |
| 27.0° ± 0.2° | 100% |
| 28.1° ± 0.2° | 58.9% |

Bulk Density: 0.61 g/mL;

Tapped Density: 0.73 g/mL;

Angle of Repose: 30.6°

Hygroscopicity Data: The test for hygroscopicity was performed as per EP general texts 5.11 page no 565. The test was performed by calculating the difference in weights, after 24-hour upon expose over a saturated solution of ammonium chloride at 25±1° C. and 80±2% relative humidity.

Hygroscopicity result: Non-hygroscopic (Increase in mass less than 0.2 percent).

| Stability Data: | | | |
|---|---|---|---|
| | Duration | | |
| | Initial | 15 days | 1 month |
| 1. Storage Condition: 25° C. ± 2° C. and 60% ± 5% Relative Humidity | | | |
| HPLC Purity | 99.9% | 99.87% | 99.91% |
| Polymorphic form | — | Unchanged | Unchanged |
| Content of Compound of Formula A | ND | ND | ND |
| Content of Compound of Formula B | ND | ND | ND |
| Content of Compound of Formula C | ND | ND | ND |
| Content of Compound of Formula D | 0.04% | 0.05% | 0.04% |
| 2. Storage Condition: 30° C. ± 2° C. and 65% ± 5% Relative Humidity | | | |
| HPLC Purity | 99.9% | 99.83% | 99.91% |
| Polymorphic form | — | Unchanged | Unchanged |
| Content of Compound of Formula A | ND | ND | ND |
| Content of Compound of Formula B | ND | ND | ND |
| Content of Compound of Formula C | ND | ND | ND |
| Content of Compound of Formula D | 0.04% | 0.05% | 0.04% |
| 3. Storage Condition: 40° C. ± 2° C. and 75% ± 5 % Relative Humidity | | | |
| HPLC Purity | 99.9% | 99.85% | 99.92% |
| Polymorphic form | — | Unchanged | Unchanged |
| Content of Compound of Formula A | ND | ND | ND |
| Content of Compound of Formula B | ND | ND | ND |
| Content of Compound of Formula C | ND | ND | ND |
| Content of Compound of Formula D | 0.04% | 0.05% | 0.04% |

ND = Not Detected

Example 2: Preparation of Crystalline Form of Compound of Formula (I)

In a 250 mL round bottom flask was added compound of Formula (I) (10 g, 24 mmol), methanol (70 mL) and water (30 mL) at 25-35° C. Sodium hydroxide (2.99 g, 74 mmol) was charged. The reaction mass was stirred at 25-35° C. for 1 hour. Water (150 mL) was charged at 25-35° C. to the reaction mixture. 15% HCl solution was added to the reaction mixture and stirred for 30-60 minutes. Reaction mass was filtered and dried at 70-75° C. to obtain 8.1 g (98%) of crystalline form of compound of Formula (I) having purity >99.80%.

Polymorphic Data (XRPD):

The X-ray powder diffraction pattern is depicted in FIG. 2.

| 2θ | Relative Intensity |
|---|---|
| 8.1° ± 0.2° | 9.1% |
| 9° ± 0.2° | 10.4% |
| 10.2° ± 0.2° | 100% |
| 10.7° ± 0.2° | 10.4% |
| 11.1° ± 0.2° | 48.6% |
| 14.6° ± 0.2° | 28.5% |
| 16.2° ± 0.2° | 11.7% |
| 17.2° ± 0.2° | 14.8% |
| 17.4° ± 0.2° | 11.3% |
| 18.9° ± 0.2° | 28.2% |
| 19.6° ± 0.2° | 29.1% |
| 21.2° ± 0.2° | 19.7% |
| 21.6° ± 0.2° | 38.1% |
| 22.5° ± 0.2° | 17.4% |
| 22.7° ± 0.2° | 12.7% |
| 23.1° ± 0.2° | 10.5% |
| 25.7° ± 0.2° | 17.6% |
| 26.5° ± 0.2° | 22.7% |
| 27° ± 0.2° | 57.4% |
| 28.1° ± 0.2° | 34.8% |
| 28.3° ± 0.2° | 13.2% |

Example-3: (1-(Cyclopropylmethoxy)-4-hydroxy-2-oxo-1,2-dihydroquinoline-3-carbonyl)glycine [Compound of Formula (I)]

In a 250 mL round bottom flask, ethyl (1-(cyclopropylmethoxy)-4-hydroxy-2-oxo-1,2-dihydroquinoline-3-carbonyl)glycinate (IX, wherein G is —COOEt) (9 g, 24 mmol) was charged to mixture of methanol (63 mL) and water (27 mL) at 25-35° C. Sodium hydroxide (2.99 g, 74 mmol) was charged. Maintained reaction at 35-45° C. for 1 hour. Water was charged at 25-35° C. after reaction completion. 15% HCl solution was charged and stirred for 30 min. Reaction mass was filtered and dried to obtain (1-(cyclopropylmethoxy)-4-hydroxy-2-oxo-1,2-dihydroquinoline-3-carbonyl)glycine (I) (8.1 g, 98%). HPLC purity >99%.

Example-4: Ethyl (1-(cyclopropylmethoxy)-4-hydroxy-2-oxo-1,2-dihydroquinoline-3-carbonyl)glycinate [Compound of Formula (IX), wherein G is —COOEt]

In a 250 mL round bottom flask, ethyl (1,4-dihydroxy-2-oxo-1,2-dihydroquinoline-3-carbonyl)glycinate (VII, wherein G is —COOEt) (14 g. 45 mmol) was charged to dimethylformamide (84 ml) at 25-35° C. under nitrogen. Potassium carbonate (8.21 g, 59 mmol), potassium iodide (0.14 g. 1%) and cyclopropylmethyl bromide (8.02 g. 59 mmol, in dimethylformamide (28 mL)) was added at 25-35° C. and stirred for 3 hours at 55-60° C. Water and conc. HCl were charged at 25-35° C. and stirred for 30 min. The solid mass was filtered and dried to obtain ethyl (1-(cyclopropylmethoxy)-4-hydroxy-2-oxo-1,2-dihydroquinoline-3-carbonyl)glycinate (IX, wherein G is —COOEt) (13.6 g, 83%).

Example-5: Ethyl (1,4-dihydroxy-2-oxo-1,2-dihydroquinoline-3-carbonyl)glycinate

[Compound of Formula (VII) wherein G is —COOEt]:

In a 250 mL round bottom flask, ethyl 1,4-dihydroxy-2-oxo-1,2-dihydroquinoline-3-carboxylate (VI, wherein R is ethyl) (11 g, 44 mmol) was charged to 1,4-dioxane at 25-35° C. Glycine ethyl ester hydrochloride (8.01 g, 57 mmol) followed by N, N-diisopropylethylamine (12.54 g, 97 mmol) were charged and the mass was stirred at 60-65° C. for 18 h. Solvent was removed at reduced pressure, water was charged to the residue and stirred. The solid mass was filtered and dried to obtain ethyl (1,4-dihydroxy-2-oxo-1,2-dihydroquinoline-3-carbonyl)glycinate (VII) (12.1 g, 90%).

Example-6: Ethyl 1,4-dihydroxy-2-oxo-1,2-dihydroquinoline-3-carboxylate [Compound of Formula (VI), wherein R is ethyl]

In a 250 mL round bottom flask, diethyl 2-(2-nitrobenzoyl) malonate (IV, wherein R is ethyl) (30 g. 97 mmol) was charged to ethanolic HCl (300 ml, 8-12% w/w). Zinc (15.85 g. 242 mmol) was charged, lot wise, to the reaction mass at 70 to −60° C., stirred for 2 h and then water was charged and stirred. The solid mass was filtered and dried to obtain ethyl 1,4-dihydroxy-2-oxo-1,2-dihydroquinoline-3-carboxylate (VI) (17.1 g, 71%).

Example-7: Ethyl 1,4-dihydroxy-2-oxo-1,2-dihydroquinoline-3-carboxylate [Compound of Formula (VI), wherein R is ethyl]

In a 250 mL round bottom flask, diethyl 2-(2-nitrobenzoyl) malonate (IV, wherein R is ethy) (100 g. 323 mmol) was charged to methanolic HCl (1000 ml, 8-10% w/w). Zinc (15.85 g, 242 mmol) was charged to reaction mass in lot wise at 65 to −60° C. and stirred for 2 h. Solvent was removed at reduced pressure; water was charged to the residue and stirred. The solid mass was filtered and dried to obtain ethyl 1,4-dihydroxy-2-oxo-1,2-dihydroquinoline-3-carboxylate (VI) (56.7 g. 71%).

Example-8: Diethyl 2-(2-nitrobenzoyl) malonate [Compound of Formula (IV), wherein R is ethyl]

In a 250 mL round bottom flask, magnesium chloride anhydrous (10.25 g. 100 mmol) was charged to acetonitrile (60 ml) at 25 to 35° C. Diethyl malonate (17.25 g. 100 mmol) and triethylamine (19.07 g. 180 mmol) were added at 0-5° C. and stirred at 25-35° C. for 1 hour. 2-Nitrobenzoyl chloride (III) in dichloromethane (30 ml) was added to reaction mass at 0-5° C. and stirred at 25-35° C. for 1 hour. Water and conc. HCl were added to the reaction mass, followed by dichloromethane and stirred. Organic layer was distilled to obtain diethyl 2-(2-nitrobenzoyl) malonate (IV) (27.6 g, 100%).

Example—9: 2-Nitrobenzoyl Chloride (III)

In a 250 mL round bottom flask, 2-nitrobenzoic acid (15 g. 89 mmol) was charged to dichloromethane (75 ml) at 25-35° C. Thionyl chloride (12.81 g. 100 mmol) and dimethylformamide (0.3 g, 2%) were added and stirred at 35-45° C. for 1 hour. Solvent was evaporated to obtain 2-nitrobenzoyl chloride (III) (16.6 g. 100%).

Example—10: Ethyl (1-(cyclopropylmethoxy)-4-hydroxy-2-oxo-1,2-dihydro-quinoline-3-carbonyl) glycinate [Compound of Formula (IX), wherein G is —COOEt]

In a 250 mL round bottom flask, ethyl (1,4-dihydroxy-2-oxo-1,2-dihydroquinoline-3-carbonyl)glycinate (VII, wherein G is —COOEt) (10 g, 45 mmol) was charged to dimethylformamide (40 ml) at 25-35° C. Cyclopropylmethyl 4-methylbenze-nesulfonate (VIII) (11.06 g, 48 mmol) and 1,8-diazabicyclo(5.4.0)undec-7-ene (6.46 g, 42 mmol) were added to the reaction mass at 0-10° C. and stirred at 25-35° C. for 18 hours. Mixture of water and conc. HCl was charged at 0-15° C. and stirred for 30 minutes. The solid mass was filtered and dried to obtain ethyl (1-(cyclopropylmethoxy)-4-hydroxy-2-oxo-1,2-dihydroquinoline-3-carbonyl)glycinate (IX) (9.7 g, 82%).

Example—11: Cyclopropylmethyl 4-methylbenzenesulfonate [Compound of Formula (VIII), wherein L is tosylate]

In a 250 mL round bottom flask, cyclopropylmethanol (5 g, 69 mmol) and p-toluene sulfonyl chloride (12.5 g, 65 mmol) were charged to dichloromethane (75 ml) at 25-35° C. Potassium hydroxide (19.44 g. 34 mmol) was added lot wise at 0-10° C. and the reaction mass was stirred at 0-10° C. for 3 hours. Water and dichloromethane were charged to reaction mass and stirred. Organic layer was distilled to obtain cyclopropylmethyl 4-methylbenzenesulfonate (VIII) (12.4 g. 80%).

Example—12: Preparation of cyclopropylmethyl chloride [Compound of Formula (VIII), wherein L is chloro]

In a 250 mL round bottom flask was added cyanuric chloride (26.85 g, 138 mmol) dichloromethane (50 ml) and dimethylformamide (30 ml) at 25-30° C. Cyclopropylmethanol (10 g. 138 mmol) was added in dichloromethane to the reaction mas at room temperature. The reaction mass was stirred for 2 hours at room temperature. Water was added to the reaction mass and the pH of the reaction mass was adjusted to 9-11 using aqueous sodium bicarbonate solution. Organic layer was separated and washed with acidic solution. The organic layer was then distilled off to obtain cyclopropylmethyl chloride. Yield: 90.8%.

Example—13: Ethyl (1-(cyclopropylmethoxy)-4-hydroxy-2-oxo-1,2-dihydro-quinoline-3-carbonyl) glycinate [Compound of Formula (IX), wherein G is —COOEt]

Ethyl (1,4-dihydroxy-2-oxo-1,2-dihydroquinoline-3-carbonyl)glycinate (VII, wherein G is —COOEt) (14 g, 45 mmol) was added to dimethylformamide (84 ml) at 25-35° C. under nitrogen environment. Potassium carbonate (8.21 g. 59 mmol), potassium iodide (0.14 g. 1%) were added to reaction mass. Cyclopropylmethyl chloride (VIII) (4.42 g, 59 mmol) in dimethylformamide was added to reaction mass at 25-35° C. Reaction was maintained at 55-60° C. for 3 hours. Water was added to the reaction mass at 25-35° C. and stirred and pH was adjusted to 2-3 using conc. HCl and stirred for 30 minutes. Reaction mass was filtered and wet cake was dried to obtain ethyl (1-(cyclopropylmethoxy)-4-hydroxy-2-oxo-1,2-dihydroquinoline-3-carbonyl)glycinate (IX) (13.6 g, 83%).

Example—14: N-(cyanomethyl)-1,4-dihydroxy-2-oxo-1,2-dihydroquinoline-3-carboxamide [Compound of Formula (VII), wherein G is —CN]

Ethyl 1,4-dihydroxy-2-oxo-1,2-dihydroquinoline-3-carboxylate (VI, wherein R is ethyl) (1 g, 40 mmol) was charged to 1,4-dioxane (4 mL) at 25-35° C. Aminoacetonitrile hydrochloride (0.4 g, 52 mmol) followed by N,N-diisopropylethylamine (1.14 g. 88 mmol) was then charged. The resultant reaction mixture was heated to 60-65° C. and maintained for 18 hours (monitored by TLC). Then 1,4-dioxane was distilled under vacuum at about 50° C. followed by degassing for 30 minutes. Water (10 mL) was then charged at 25-35° C. and stirred for 1 hour. Solid was filtered followed by washing with water (2×5 mL). Wet cake was dried at 70-75° C. under vacuum to obtain N-(cyanomethyl)-1,4-dihydroxy-2-oxo-1,2-dihydroquinoline-3-carboxamide (0.72 g, 98%).

Mass Spectrometry Analysis

Mass (ESI-MS) m/z calculated for $C_{12}H_9N_3O_4$ $[M+H]^+$ 260.06 and found 260.1.

NMR Spectrometry Analysis $^1H$ NMR (400 MHZ, DMSO-$d_6$): δ 15.992 (bs, 1H), 11.396 (bs, 1H), 10.452 (s, 1H), 8.109-8.086 (dd, 1H, J=1.2 & 8), 7.869-7.827 (m, 1H), 7.744-7.723 (d, 1H, J=8.4), 7.405-7.369 (t, 1H, J=7.2), 4.485-4.470 (d, 2H, J=6).

Example 15: N-(cyanomethyl)-1-(cyclopropylmethoxy)-4-hydroxy-2-oxo-1,2-dihydro quinoline-3-carboxamide [Compound of Formula (IX), wherein G is —CN]

N-(cyanomethyl)-1,4-dihydroxy-2-oxo-1,2-dihydroquinoline-3-carboxamide (VII, wherein G is —CN) (0.715 g, 27 mmol) was charged to dimethylformamide (5.72 mL) at 25-35° C. Potassium carbonate (0.495 g. 35 mmol), potassium iodide (0.01 gm, 1 mol %) was then charged followed by addition of cyclopropyl methylbromide (0.484 g. 35 mmol) at 25-35° C. The resultant reaction mass was then heated to 60-70° C. and maintained for 3 hours (monitored by TLC). Mixture of water (20 mL) and conc. HCl (2 mL) was charged into reaction mass at 25-35° C. and stirred for 30-40 minutes. Solid was filtered followed by washing with water (2 mL). The wet cake was dried at 70-75° C. under vacuum to obtain N-(cyanomethyl)-1-(cyclopropylmethoxy)-4-hydroxy-2-oxo-1,2-dihydro quinoline-3-carboxamide (0.74 g, 85%).

Mass Spectrometry Analysis

Mass (ESI-MS) m/z calculated for $C_{16}H_{15}N_3O_4$ $[M+H]^+$ 314.11 and found 314.1.

NMR Spectrometry Analysis $^1H$ NMR (400 MHZ, DMSO-$d_6$): δ 16.257 (s, 1H), 10.311 (s, 1H), 10.452 (s, 1H), 8.108-8.088 (d, 1H, J=8), 7.879 (s, 1H), 7.719-7.698 (d, 1H, J=8.4), 7.416 (s, 1H), 4.458-4.443 (d, 2H, J=6), 4.047-4.029 (d, 2H, J=7.2), 1.285 (s, 1H), 0.605-0.590 (d, 2H, J=6), 0.390-0.375 (d, 2H, J=6).

Example 16: (1-(cyclopropylmethoxy)-4-hydroxy-2-oxo-1,2-dihydroquinoline-3-carbonyl)glycine [Compound of Formula (I)]

N-(cyanomethyl)-1-(cyclopropylmethoxy)-4-hydroxy-2-oxo-1,2-dihydroquinoline-3-carboxamide (IX, wherein G is —CN) (0.10 g, 3 mmol) was charged to methanol (1 mL) and water (1 mL), followed by sodium hydroxide (0.08 g, 16 mmol) at 25-35° C. The resultant reaction mass was stirred at 25-35° C. for 24 hours (monitored by TLC). Water (3 mL)

and Conc. HCl (0.7 mL) was then charged at 25-35° C. and stirred for 30-40 minutes. Solid was filtered on Whatman grade-1 filter paper (11μ) and cloth under suction followed by water washing (1 mL). The wet cake was dried at 70-75° C. under vacuum (9 mbar) for 5 hours to obtain (1-(cyclopropylmethoxy)-4-hydroxy-2-oxo-1,2-dihydroquinoline-3-carbonyl)glycine (0.098 g, 92%).

While the present invention has been described in terms of a few specific embodiments, modification and equivalents thereof, in light of the teaching and disclosure of the present invention, that are apparent to the skilled artisan, are to be construed as included within the scope of the invention.

We claim:

1. A crystalline form of compound of Formula (I), (I)

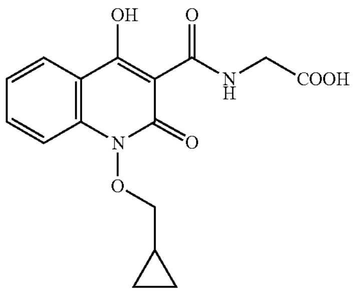

characterized by X-ray powder diffraction pattern having at least four peaks expressed in degrees 2θ+0.2° selected from 10.2°, 11.1°, 14.6°, 18.9°, 19.6°, 21.6°, 27.0° and 28.1°.

2. The crystalline form of the compound of Formula (I) according to claim 1, further characterized by X-ray powder diffraction pattern having peaks expressed in degrees 2θ+0.2° at 10.2°, 11.1°, 14.6°, 18.9°, 19.6°, 21.6°, 27.0° and 28.1°; or a X-ray powder diffraction pattern substantially same as depicted in FIG. 1.

3. The crystalline form of the compound of Formula (I) according to claim 1, (I)

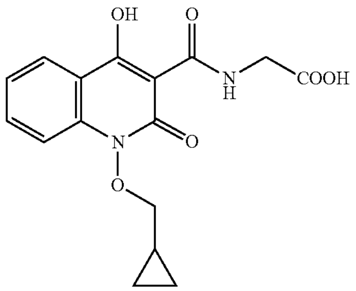

characterized by X-ray powder diffraction pattern having peaks expressed in degrees 2θ+0.2° at 8.1°, 9.0°, 10.2°, 11.1°, 14.6°, 18.9°, 19.6°, 21.6°, 27.0° and 28.1°; or a X-ray powder diffraction pattern substantially same as depicted in FIG. 2.

4. The crystalline form of the compound of Formula (I) according to claim 3, wherein the peak expressed in degrees 2θ at) 10.2° (+0.2° is having at least about 25% relative intensity; and the peaks at 11.1° and) 27.0° (+0.2° exhibit at least about 35% intensity relative to the intensity of the peak at) 10.2° (+0.2°.

5. A process for the preparation of the crystalline form of compound of Formula (I) according to claim 1, the process comprising:

(a) obtaining a solution of the compound of Formula (I) in a solvent mixture comprising halogenated solvent and a polar solvent; and (b) removing the solvent from the solution to obtain the crystalline form of compound of Formula (I).

6. The process according to claim 5, wherein the halogenated solvent at step (a) is selected from methylene dichloride, ethylene dichloride, chloroform and carbon tetrachloride, or mixtures thereof; and the polar solvent at step (a) comprises one or more of alcohols, ketones, esters and ethers; wherein the alcohol is selected from methanol, ethanol, propan-2-ol, butanol, pentanol, ethylene glycol, propylene glycol and glycerol, or mixtures thereof; wherein the ketone is selected from acetone, methyl ethyl ketone, methyl isobutyl ketone, methyl amyl ketone, cyclohexanone and diisobutyl ketone, or mixtures thereof;

the ester is selected from methyl acetate, ethyl acetate, isopropyl acetate, n-butyl acetate, sec-butyl acetate, tert-butyl acetate, isobutyl acetate, isoamyl acetate and hexyl acetate, or mixtures thereof; and the ether is selected from tetrahydrofuran, 2-methyltetrahydrofuran, 1,4 dioxane, diisopropyl ether, methyl tert-butyl ether and morpholine, or mixtures thereof.

7. The process according to claim 5, wherein the removal of the solvent at step (b) is carried out by distillation, evaporation, evaporation under reduced pressure, or evaporation under vacuum.

8. The process according to claim 5, wherein the solvent mixture at step (a) is a mixture of halogenated solvent and alcohol solvent.

9. A process for the preparation of a compound of Formula (I), (I)

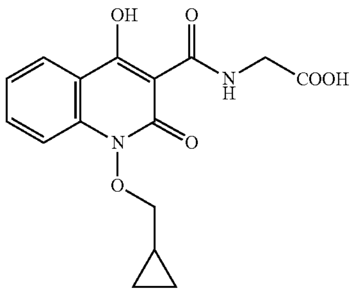

the process comprising:

(a) reacting a compound of Formula (VII), (VII)

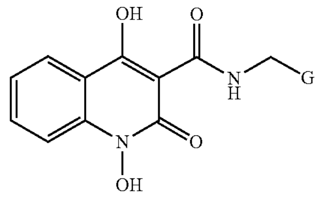

with a compound of Formula (VIII), (VIII)

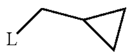

wherein,

L is a leaving group;

to obtain a compound of Formula (IX);

(IX)

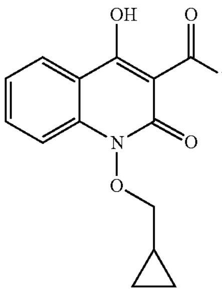

wherein,

G is selected from —CN, —COORa and —CONRbRc;

Ra is selected from alkyl, cycloalkyl, heterocycloalkyl, aryl and heteroaryl; wherein Ra is optionally further substituted with one or more of chloro, bromo, iodo, cyano, hydroxy, nitro, amino, alkylamino, carbonyl, aminocarbonyl, thio, alkylthio, alkyl, cycloalkyl, heterocycloalkyl, aryl or heteroaryl; and Rb and Rc each independently is hydrogen or Ra;

and, (b) converting the compound of Formula (IX) to the compound of Formula (I).

10. The process according to claim 9, wherein the leaving group L in the compound of Formula (VIII) is selected from halogens, sulfonate esters and perfluoroalkylsulfonates.

11. The process according to claim 9, wherein the step (a) is carried out in the presence of a base in one or more solvents; wherein the base is selected from organic bases comprising triethylamine, diisopropylethylamine, piperidine, 4-dimethylamino pyridine (DMAP), 1,8-diazabicyclo [5.4.0]undec-7-ene (DBU), 1,5-diazabicyclo-[4.3.0]non-5-ene (DBN), 1,4-diazabicyclo [2.2.2]octane (DABCO), N-methylmorpholine, N-methyl pyrrolidine, or mixtures thereof; or inorganic bases comprising potassium hydroxide, sodium hydroxide, lithium hydroxide, calcium hydroxide, magnesium hydroxide, sodium carbonate, lithium carbonate, potassium carbonate, cesium carbonate, sodium bicarbonate, potassium bicarbonate, sodium hydride, sodium methoxide, potassium methoxide, sodium tert-butoxide, and potassium tert-butoxide, or mixtures thereof; and wherein the solvent is selected from N,N-dimethylformamide (DMF), dimethylacetamide, dimethyl sulfoxide, tetrahydrofuran, ethyl acetate, acetonitrile, toluene, xylene, isopropyl acetate, 2-methyltetrahydrafuran, 1,4-dioxane, acetone, or mixtures thereof.

12. The process according to claim 9, wherein the step (b) is carried out by hydrolyzing the compound of Formula (IX) in the presence of an acid or a base.

13. The process according to claim 9, wherein G in the compound of Formula (VII) and (IX) is —CN or —COORa, wherein Ra is C1-4 alkyl.

14. A compound of Formula (VII), (VII)

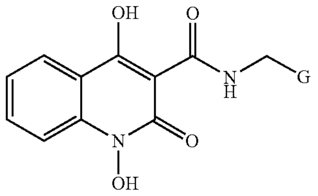

wherein,

G is selected from —CN, —COORa and —CONRbRc,

Ra is selected from alkyl, cycloalkyl, heterocycloalkyl, aryl and heteroaryl; wherein Ra is optionally further substituted with one or more of chloro, bromo, iodo, cyano, hydroxy, nitro, amino, alkylamino, carbonyl, aminocarbonyl, thio, alkylthio, alkyl, cycloalkyl, heterocycloalkyl, aryl or heteroaryl; and Rb and Rc each independently is hydrogen or Ra.

15. The compound of Formula (VII) according to claim 14, wherein G is —CN or —COORa, wherein Ra is C1-4alkyl.

16. A process for the preparation of the compound of Formula (VII) according to claim 14, the process comprising:

(a) converting a compound of Formula (IV), (IV)

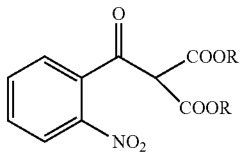

to a compound of Formula (VI), (VI)

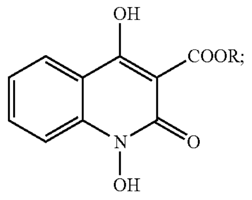

and, (b) reacting the compound of Formula (VI) with a compound of Formula (X)

(X)

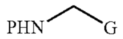

to obtain the compound of Formula (VII);

wherein, each R is independently selected from alkyl and aryl,

P is selected from hydrogen or amino protecting group;

G is selected from —CN, —COORa and —CONRbRc,

Ra is selected from alkyl, cycloalkyl, heterocycloalkyl, aryl and heteroaryl; wherein Ra is optionally further substituted with one or more of chloro, bromo, iodo, cyano, hydroxy, nitro, amino, alkylamino, carbonyl, aminocarbonyl, thio, alkylthio, alkyl, cycloalkyl, heterocycloalkyl, aryl or heteroaryl; and Rb and Rc each independently is hydrogen or Ra.

17. The process according to claim 16, wherein the step (a) is carried out by reacting the compound of Formula (IV) with zinc and alcoholic hydrochloric acid.

18. The process according to claim 16, wherein the step (b) is carried out in the presence of a base in one or more solvents; wherein the base is selected from organic bases comprising triethylamine, diisopropylethylamine, piperidine, 4-dimethylaminopyridine (DMAP), 1,8-diazabicyclo [5.4.0]undec-7-ene (DBU), 1,5-diazabicyclo [4.3.0]non-5-ene (DBN), 1,4-diazabicyclo [2.2.2]octane (DABCO), N-methylmorpholine, N-methyl pyrrolidine, or mixtures thereof; or inorganic bases comprising potassium hydroxide, sodium hydroxide, lithium hydroxide, calcium hydroxide, magnesium hydroxide, sodium carbonate, lithium carbonate, potassium carbonate, cesium carbonate, sodium bicarbonate, potassium bicarbonate, sodium hydride, sodium methoxide, potassium methoxide, sodium tert-butoxide, and potassium tert-butoxide, or mixtures thereof; and the solvent is selected from N,N-dimethylformamide (DMF), dimethylacetamide, dimethyl sulfoxide, tetrahydrofuran, ethyl acetate, acetonitrile, toluene, xylene, isopropyl acetate, 2-methyltetrahydrafuran, 1,4-dioxane, acetone, or mixtures thereof.

19. The process according to claim 16, wherein R is $C_{1-4}$ alkyl; P is hydrogen and G is CN or —COORa, wherein Ra is $C_{1-4}$ alkyl.

20. A composition comprising a compound of Formula (I)

(I)

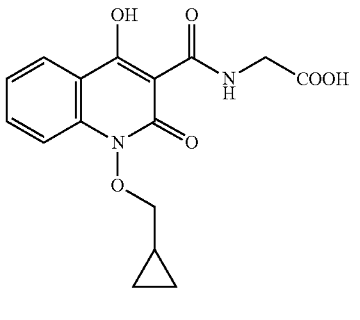

having a purity of about 99% or more, and one or more of compounds of Formulae C, D or E in an amount less than about 0.15% by area percentage of HPLC relative to the compound of Formula (I), (C)

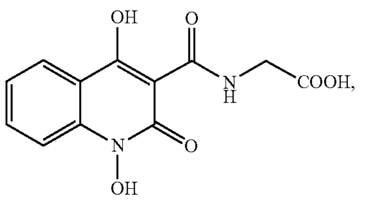

-continued (D)

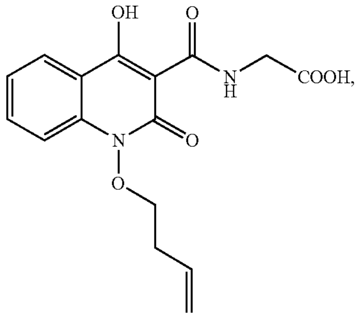

(E)

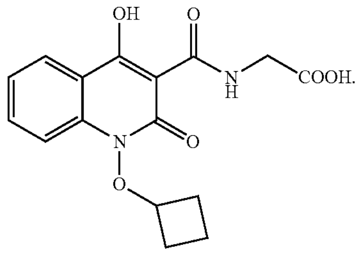

21. The composition according to claim 20, wherein the compound of Formula D is present in an amount less than about 0.15% by area percentage of HPLC relative to the compound of Formula (I), and the compound of Formula E is present in an amount less than about 0.15% by area percentage of HPLC relative to the compound of Formula (I).

22. A composition comprising a crystalline form of compound of Formula (I) according to claim 1, having a purity of about 99% or more and one or more of compounds of Formulae A, B, C, D or E in an amount less than about 0.15% by area percentage of HPLC relative to the compound of Formula (I), (A)

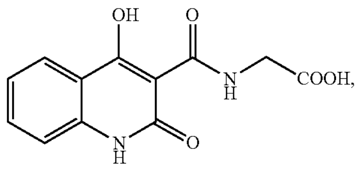

(B)

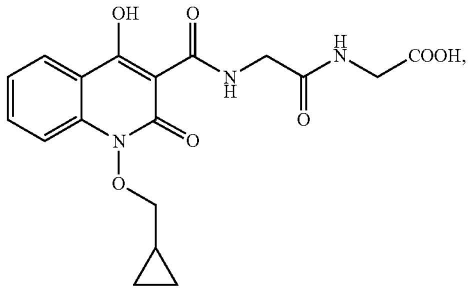

-continued (C)

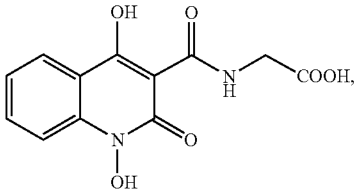

(D)

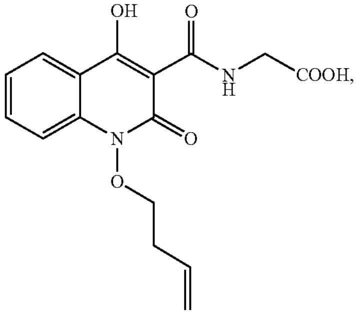

-continued (E)

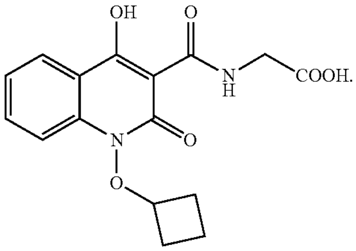

23. The composition according to claim 22, wherein the compound of Formula D is present in an amount less than about 0.15% by area percentage of HPLC relative to the compound of Formula (I) and the compound of Formula E is present in an amount less than about 0.15% by area percentage of HPLC relative to the compound of Formula (I).

24. The crystalline form of the compound of Formula (I) according to claim 1, for use in the preparation of a pharmaceutical composition comprising the crystalline form of compound of Formula (I) according to claim 2 and one or more pharmaceutically acceptable carriers, diluents and excipients.

25. The crystalline form of the compound of Formula (I) according to claim 24, wherein the pharmaceutical composition prepared is administered to a patient in need thereof for the treatment of anemia.

* * * * *